US009909128B2

(12) United States Patent
Walker et al.

(10) Patent No.: US 9,909,128 B2
(45) Date of Patent: Mar. 6, 2018

(54) SPLICE MODULATING OLIGONUCLEOTIDES THAT INHIBIT CANCER

(71) Applicant: The Regents of the University of California, Oakland, CA (US)

(72) Inventors: Ameae Walker, Riverside, CA (US); Mrinal Ghosh, Lancaster, CA (US); Kuan-Hui Chen, Riverside, CA (US); Tomohiro Yonezawa, Tokyo (JP)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/443,360

(22) PCT Filed: Nov. 15, 2013

(86) PCT No.: PCT/US2013/070445
§ 371 (c)(1),
(2) Date: May 15, 2015

(87) PCT Pub. No.: WO2014/078749
PCT Pub. Date: May 22, 2014

(65) Prior Publication Data
US 2015/0337310 A1    Nov. 26, 2015

Related U.S. Application Data

(60) Provisional application No. 61/727,030, filed on Nov. 15, 2012.

(51) Int. Cl.
| C12N 15/117 | (2010.01) |
| C12N 15/11 | (2006.01) |
| A61K 48/00 | (2006.01) |
| C07H 21/04 | (2006.01) |
| C12N 15/113 | (2010.01) |

(52) U.S. Cl.
CPC .......... *C12N 15/117* (2013.01); *C12N 15/113* (2013.01); *C12N 15/1138* (2013.01); *C12N 2310/11* (2013.01); *C12N 2310/17* (2013.01); *C12N 2310/3233* (2013.01); *C12N 2310/351* (2013.01); *C12N 2320/33* (2013.01)

(58) Field of Classification Search
CPC .............. C12N 15/113; C12N 15/1138; C12N 2310/11; C12N 2310/17; C12N 2310/3233; C12N 2320/33; A61K 48/00
USPC .................... 435/6.1, 6.11, 91.1, 91.31, 455; 424/278.1; 514/44; 536/23.1, 24.5
See application file for complete search history.

(56) References Cited

U.S. PATENT DOCUMENTS

| 4,469,863 | A | 9/1984 | Ts'o et al. |
| 5,750,666 | A | 5/1998 | Caruthers et al. |
| 2003/0194704 | A1 | 10/2003 | Penn et al. |
| 2009/0123428 | A1 | 5/2009 | Hall et al. |
| 2013/0046007 | A1* | 2/2013 | Bennett ................ C12N 15/113 514/44 A |
| 2014/0249210 | A1* | 9/2014 | Lutz ..................... A61K 48/005 514/44 R |
| 2015/0080452 | A1* | 3/2015 | Thornton ............. C12N 15/113 514/44 A |

FOREIGN PATENT DOCUMENTS

WO    2010083338 A2    7/2010

OTHER PUBLICATIONS

Clavenger et al, Trends in Endocrinology and Metabolism, vol. 20, No. 5, pp. 223-229 (2009).*
Trott et al, J. Molec. Endocrin., vol. 30, pp. 31-47 (2003).*
Clancy, S. et al. Nature Education 1 (1) 92008) and Black, D. Annual Reviews of Biochemistry (2003)72(1) 291-336.
Patel A. and Steitz J. Nat. Rev. Mol. Cell Biol. (2003) 4(12): 960-70.
Wang, E. et al. Nature (2008) 456:470-476.
Smirnova, O. et al. Biochemistry (Moscow) (2004) 59:351-363.
Hertel, K. et al. J Biol Chem (2008) 283:1211-1215.
Lin, S. et al. Adv Exp Med Biol (2007) 623:107-122.
Martinez-Contreras, R. et al. Adv Exp Med Biol (2007) 623:123-147.
K. Hung, R. Hayashi, A. Lafond-Walker, C. Lowenstein, D. Pardoll, and H. Levitsky, "The central role of CD4+ T cells in the antitumor immune response." J. Exp. Med., 188(12):2357-2368, 1998.
A. Corthay, D. K. Skovseth, K. U. Lundin et al., "Primary antitumor immune response mediated by CD4+ T cells," Immunity, 22(3): 371-383. 2005.
A. Perez-Diez, N. T. Joncker, K. Choi et al., "CD4 cells can be more efficient at tumor rejection than CD8 cells," Blood, 109(12): 5346-5354, 2007.
K. Rakhra, P. Bachireddy, T. Zabuawala et al., "CD4+ T cells contribute to the remodeling of the microenvironment required for sustained tumor regression upon oncogene inactivation," Cancer Cell. 18(5): 485-498, 2010.

(Continued)

Primary Examiner — Jane J Zara
(74) Attorney, Agent, or Firm — Berliner & Associates

(57) ABSTRACT

A method of treating cancer in a subject is provided. The method includes administering a splice modulating oligonucleotide to the subject in an amount effective to provide a therapeutic benefit to the subject. In the method, the oligonucleotide modifies splicing of a pre-mRNA encoding a polypeptide, and either: reduces expression of the polypeptide if the polypeptide promotes cancer cell survival, proliferation, and/or metastasis, or promotes angiogenesis, or a combination thereof; or increases expression of the polypeptide if the polypeptide inhibits cancer cell survival, proliferation and/or metastasis, or inhibits angiogenesis, or a combination thereof. Similar methods of treating diseases involving prolactin or the prolactin receptor are also provided.

30 Claims, 15 Drawing Sheets

(56) References Cited

OTHER PUBLICATIONS

J.R. Schoenborn and C.B. Wilson. "Regulation of interferon-gamma during innate and adaptive immune responses", Adv. Immunol., 95: 41-101. 2007.
K.A. Smith. "Interleukin-2: inception, impact, and implication", Science. 240(4656): 1169-1176, 1968.
Tworoger SS, Eliassen AH. Sluss P, Hankinson SE. J Clin Oncol. 2007 ;25(12):1482-6.
Clevenger CV, Chang WP, Ngo W, Pasha TL, Montone KT, Tomaszewski JE. Am J Pathol. 1995 ;146(3):695-705.
Gill S. Peston D, Vonderhaar BK, Shousha S, J Clin Pathol. Dec. 2001;54(12):956-60.
Greendale GA, Huang MH, Ursin G, Ingles S, Stanczyk F. Crandall C, Laughlin GA, Barrett-Connor E, Karlamangla A, Breast Cancer Res Treat. Nov. 2007;105(3):337-46.
Boyd NF. Stone J, Martin LJ. Jong R, Fishell E, Yaffe M, Hammond G. Minkin S Br J Cancer, Oct 7, 2002;87 (8):676-82.
Shemanko CS. Mammary epithelial stem and progenitor cells and the protactin pathway. Front Biosci, 13:3940-50, 2006.
Cleveriger CV, Gadd SI, Zheng J. Trends Endocrinol Metab 20: 223-9,2009.
Pujianto DA, Curry BJ, Aitken RJ. Endocrinology 151: 1269-79,2010.
Ormandy CJ, Binart N, Helleco C. Kelly PA. DNA Cell Biol 17:761-70, 1998.
Meng J. Tsai-Morris CH. Dufau M. Cancer Res 64:5677-82,2004.
Huang K, Ueda E, Chen Y, Walker AM. J Mammary Gland Biol Neoplasia. 2008;13(1):69-79.
Tan D. Walker AM. J Mol Endocrinology 44:187-94. 2010.
Trott et al., "Alternative splicing to exon 11 of human prolactin receptor gene results in multiple isoforms including a secreted prolactin-binding protein"; J Mol Endocrinol. 2003, vol. 30(1), p. 31-47.
GenBank_AF042358, Ovis aries prolactin receptor short form and long form genes, partial cds, Jan. 26, 1998, Accession Number: AF042358; (online), retrieved on Dec. 26, 2013 from the internet: URL: http://www.ncbi.nim.nih.gov/nuccore/AF042348: Source; Intron; Origin, sequence (826 nt)—nucleotides between 826-802.
Perez-Diez et al "CD4 cells can be more efficient at tumor rejection than CD8 cells.", Blood 2007, vol. 109(12), p. 5346-54.
Meng et al, Human Prolactin Receptor Variants in Breast Cancer: Low Ratio of Short Forms to the Long-Form Human Prolactin Receptor Associated with Mammary Carcinoma. Cancer Res. 2004, vol. 64 (16), p. 5677-82.

\* cited by examiner

Figure 1A

Sequence of Estrogen Receptor – alpha precursor mRNA exon 5 (capital letters and 150 bp of flanking introns (small letters)

uacuugacuucacuauaaaguauguucuauugcauuuacuccaucuaguagaaaauagaccuugucaguucaaaucc
cuguugcauuaauuucaccaguaaugaguucuuuuucauuugagucagcagggunnuucuugcuuguauuucagGCUUUG
UGGAUUUGACCCUCCAUGAUCAGGUCCACCUUCUAGAAUGUGCCUGGCUAGAGAUCCUGAUGAUUGGUCUCGUCUGGC
GCUCCAUGGAGCACCCAGGGAAGCUACUGUUUGCUCCUAACUUGCUCUUGGACAGguaaguaaccuggcuguagcuua
ggaguagcauguucuuuacgaucauaguucauucaugaaacuauuuuauucaucucucggugaagcuucagagaacuu
uauuagguauguuuacuuaacaaaagagugcauuggggugaugaagcc    SEQ ID NO:1

Figure 1B

Sequence of Estrogen Receptor – alpha precursor mRNA exon 7 (capital letters and 150 bp of flanking introns (small letters)

cgguuuuaaaugggucagagcaucccauugcuagacuacugugcugaggaagggcacugcucauuguuacauccca
ugaacacucugggucuccuagaccucauccucuuugagcuucucucucucacucucucugcgcauucagGAGUGUAC
ACAUUUCUGUCCAGCACCCUGAAGUCUCUGGAAGAGAAGGACCAUAUCCACCGAGUCCUGGACAAGAUCACAGACACUU
UGAUCCACCUGAUGGCCAAGGCAGGCCUGACCCUGCAGCAGCAGCACCAGCGGCUGGCCCAGCUUCUCCUCAUCCUCUC
CCACAUCAGGCACAUGAGgugaggcaucugugggcuuccuacaggagagacauaaagaaaacaugccccaaaccuaug
ugacagcuggccgggaaggacuggugccugcauaggagagugcacuugacaguucuggcauagaauaagcauaaa
ugcuauaggaggaca    SEQ ID NO:2

Figure 1C

Sequence of Estrogen Receptor – alpha SMO Target Sequence 1

UCUCACUCUCUCUCUGCGCAUUCAGGAGUGUACACAUUUCUGUCCAGCAC    SEQ ID NO:3

Sequence of Estrogen Receptor – alpha SMO Target Sequence 2

UCCUCUCCCACAUCAGGCACAUGAGGUGAGGCAUCUGUGGGCUUCCUACA    SEQ ID NO:4

Sequence of Estrogen Receptor – alpha SMO Target Sequence 3

UGCUAGACUACUGUGC    SEQ ID NO:5

Sequence of Estrogen Receptor – alpha SMO Target Sequence 4

CCAUGAACACUCUGGGUCUCCUAGACCUCAUCCUCUUUGAGCUUCUCUCUCUCACUCUCUCUGCG
SEQ ID NO:6

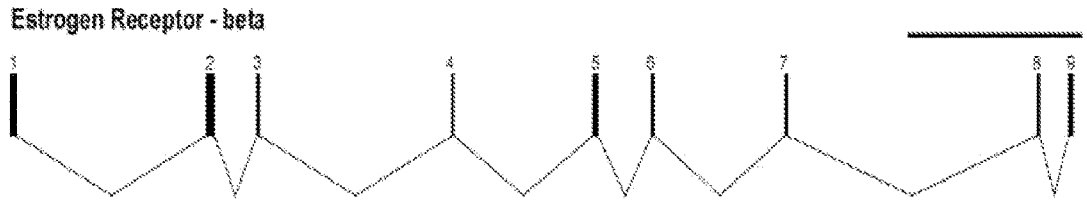

Estrogen Receptor - beta

Figure 2A

Sequence of Estrogen Receptor – beta precursor mRNA exon 5 (capital letters and 150 bp of flanking introns (small letters)

aaaaguuauguucguuugguuuuugcuaguacggucacgaccauaguaaucuuugguacgugccccacaggcuccagaa
aauaaaagucaagcugcuuuugcuugacugcgguuuuacccuggcaauucgaaugacucugcuuuccucuucagGC
UCCCGGAGAGAGACAUGUGGGUACCGCCUUGUGCGGAGACAGAGAAGUGCCGACGAGCAGCUGCACUGUGCCGGCA
AGGCCAAGAGAAGUGGCGGCCACGCGCCCGAGUGCGGGAGCUGCUGCUGGACGCCCUGAGCCCCGAGCAGCUAGU
GCUCACCCUCCUGGAGGCUGAGCCGCCCCAUGUGCUGAUCAGCCGCCCCAGUGCGCCCUUCACCGAGGCCUCCAUG
AUGAUGUCCCUGACCAAGUUGGCCGACAAGGAGUUGGUACACAUGAUCAGCUGGGCCAAGAAGAUUCCCGguaggg
cuuucuggcuaucaguuuuccauguacuuguagaaaggccggccgcuaauauuuaaggggcaagaguacaaaguag

SEQ ID NO:7

Figure 2B

Sequence of Estrogen Receptor – beta SMO Target Sequence 1

CGAAUGACUCUGCUUUCCUCUUCAGGCUCCCGGAGAGAGACAUGUGGGUA   SEQ ID NO: 8

Sequence of Estrogen Receptor – beta SMO Target Sequence 2

AUCAGCUGGGCCAAGAAGAUUCCCGGUAGGGCUUUCUGGCUAUCAGUUUU   SEQ ID NO:9

Sequence of Estrogen Receptor – beta SMO Target Sequence 3

CACGACCA   SEQ ID NO:10

Sequence of Estrogen Receptor – beta SMO Target Sequence 4

UCUGCUUUCCUCU   SEQ ID NO:11

STAT5a

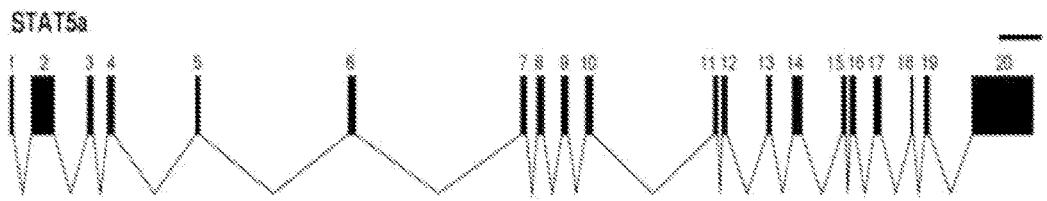

Figure 3A

Sequence of STAT5a precursor mRNA exon 5 (capital letters
and 150 bp of flanking introns (small letters)

acagagauauagaggugucuggggauaguuccugagcucccugggaaaagcugadgcagaggcugaaggagaggaaggg
cugggcauagcaugggcuggcauggcuggagcagaggauggcgcuggaggcuacuguuggauucuuucaGAAAACAUAU
GACCGCUGCCCCCUGGAGCUGGUCCGCUUGCAUCCGGCACAUUCUGUACAAUGAACACAGGCUGGUCCGACAAGCCAACAA
UGuyagugucccuuggggauggggaggagugungagaagucccuccauaugccuuucucuccagaaacaacuguguuuau
auaaaacagcagcacgaggagagcaccaagaagaugagggacguggcaaguguaagaggucggcagcauugca

SEQ ID NO:12

Figure 3B

Sequence of STAT5a SMO Target Sequence 1

GGGGCACUACGCCACGCAGCUCCAG    SEQ ID NO:13

Sequence of STAT5a SMO Target Sequence 2

UGCAGCUCUCGGCUGGGAUCCUGG    SEQ ID NO:14

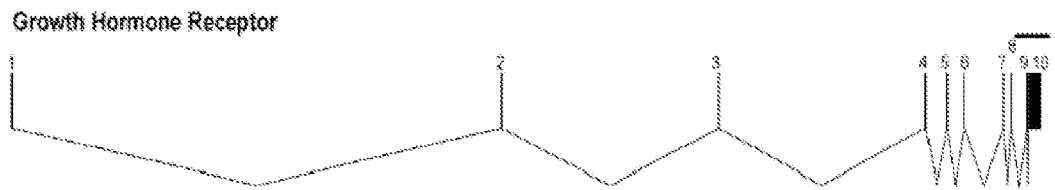

Figure 4A

Sequence of Growth Hormone Receptor precursor mRNA exon 8 (capital letters and 150 bp of flanking introns (small letters)

ucauaaaacagaaaaaaacuaagucguugcauucuguuucaguggvuaucaagagaaaaucacugacuuuauuagaugaau
acaaauuaugaauuuuuuugugaaaagggaaagggaaauguaaacugugcuucaacuauucguaauucugaAUUUCUACUU
UCCAUGGCUCUUAAUUAUUAUCUUUGGAAUAUUUGGGCUAACAGUGAUGCUAUUUGUAUUCUUAUUUUCUAAACAGCAAA
Gguaggugugguaguauucuuugguauuuuguaccaguuguuuagauuuccauaugugvuuucuauugvuauuugaua
uuuucuuugucaaauuaugaguggaaauuuuaguuaaccaguacacuuuuaucuccaguuauauauuuac

SEQ ID NO:15

Figure 4B

Sequence of Growth Hormone Receptor precursor mRNA exon 9 (capital letters and 150 bp of flanking introns (small letters)

uaguugvucuuuuuuuuuccuucuacaguuuuacuuucucauuuacugvucuaauauuuucuucuguuucucacacuccaau
uauauaaaguaccagaauauuuggaaaaaguaauaguauugccaauauuuuauuucuaucuuuugcuauaGAUUAAAAUG
CUGAUUCUGCCCCAGUUCCAGUUCCAAAGAUUAAAGGAAUCGAUCCAGAUCUCCUCAAGguaacuaauaauuuuaucua
aauuguagcuaguacuaauuaacaccugaagacuccugucauauguugaagguuuucuguaagcuauauauaucacauuc
aauuuucuguguucucuucuccuggagaaauuuuuuuaaauauucuauu

SEQ ID NO:16

Figure 4C

Sequence of Growth Hormone Receptor SMO Target Sequence 1

AACCAAAAUUUUAUAUGUUUUCAAGGAUUAAAAUGCUGAUUCUGCCCCA   SEQ ID NO:17

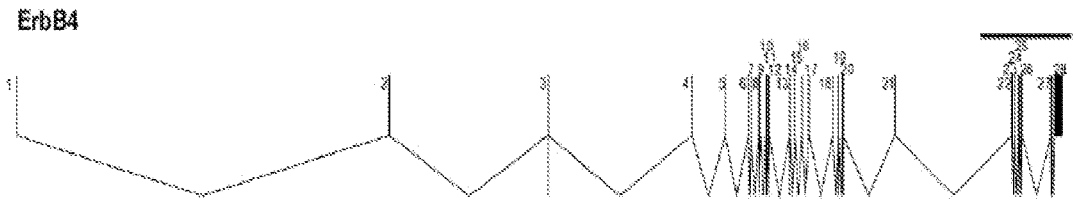

Figure 5A

Sequence of ErbB4 precursor mRNA exon 26 (capital letters and 150 bp of flanking introns (small letters)

auugugcugcuuaggaagcuucacuguugugcacuuuuucccuuugguucauacgacccauguggcuuuucuuuuucgu
uucuuuuuuaauuuuuucauucauauugccucuuauuauauccaucauccauuuuucuuuccuauuagAGUGAAAUUG
GACACAGCCCUCCUCCUGCCUACACCCCCAUGUCAGGAguaaguauuucacaaucaaccuucaucuuuuaggauuuucgg
ucuuugcuuaccauguuuccucucucgucucugcauaauuuccucauuuugccuuugccaacagugaguuaagaauuugg
uguacaucguguagcugccuuuguagau

SEQ ID NO:18

Figure 5B

Sequence of ErbB4 SMO Target Sequence 1

UCAUUCCAUUUUUCUUUCCUAUUAGAGUGAAAUUGGACACAGCCCUCC   SEQ ID NO:19

Sequence of ErbB4 SMO Target Sequence 2

UCCUGCCUACACCCCCAUGUCAGGAGUAAGUAUUUCACAAUCAACCUUCA   SEQ ID NO:20

Sequence of ErbB4 SMO Target Sequence 3

GGCUUUUCUUUUUCGUUUCUU   SEQ ID NO:21

Sequence of ErbB4 SMO Target Sequence 4

UCAUUCAUAUUGCCUCUU   SEQ ID NO:22

Sequence of ErbB4 SMO Target Sequence 5

CCAUCAUUCCAUUUUUCUUU   SEQ ID NO:23

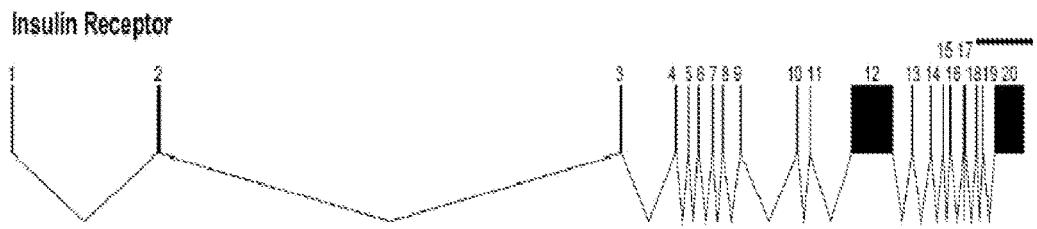

Figure 6A

Sequence of Insulin Receptor precursor mRNA exon 11 (capital letters and 150 bp of flanking introns (small letters)

ccugcaccugcugggaagauguagcucacuccgucuagcaagugaugggagcgaguggiccagggucaaagccagggug
cccuuacucggacacaugiggccuccaagugucagagccaguggucugucaaugaaguucccucuguсAAAACCUCU
UCAGGCACUGGUGCCGAGGACCUAGguaugacucaccugugcgaccccuggugccugcuccgcgcagggccggcggcgu
gccaggcagaugccucggagaacccaggggiuuucugiggcuuuuugcaugcggcgggcagcugiugcuggagagcagaugc
uucaccaauucagaaa

SEQ ID NO:24

Figure 6B

Sequence of Insulin Receptor SMO Target Sequence 1

UGCACAACGUGGUUUUCGUCCCAG    SEQ ID NO:25

Sequence of Insulin Receptor SMO Target Sequence 2

GCCAUCUGGAAACGCAGGUCCUU    SEQ ID NO:26

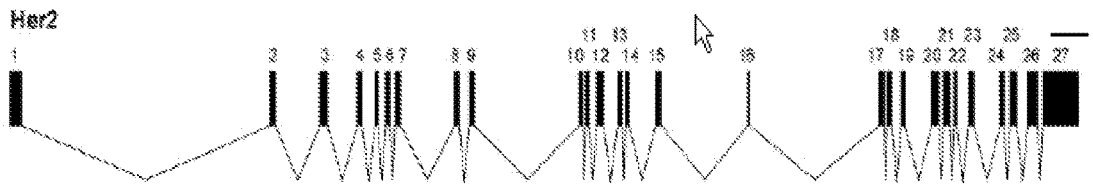

Figure 7A

Sequence of Her2 precursor mRNA exon 16 (capital letters and 150 bp of flanking introns (small letters)

ccugcaccugcugggaagauguagcucacuccgucuagcaagugaugggagcgagugguccaggggucaaagccaggggug
cccuuacucggacacauguggccuccaagugucagagccaguggucuguc uaaugaaguuccucuguc AAAAACCUCU
UCAGGCACUGGUGCCGAGGACCCUAGguaugacucaccugugcacccuggugccugcuccgcgcaggg ccggcggcgu
gccaggcagaugccucggagaacccaggggguuucugugg cuuuuugcaugcggcgggcagcugugcug gagagcagaugc
uucaccaauucagaaa

SEQ ID NO:27

Figure 7B

Sequence of Her2 precursor mRNA exon 1

GGAGGAGGUGGAGGAGGAGGGCUGCUUGAGGAAGUAUAAGAAUGAAGUUGUGAAGCUGAGAUUCCCUCCAUUGGGACCG
GAGAAACCAGGGGAGCCCCCGGCCAGCCGCGCGCCCUUCCCACGGGGCCCUUUACUGCGCCGCGCGCCCGGCCCCCAC
CCCUCGCAGCACCCCGCGCCCGGCCCUCCCAGCCGGGUCCAGCGGGAGCCAUGGGGCCGGAGCCGCAGUGAGCACCAU
GGAGCUGGCGGCCUUGUGCCGCUGGGGGCUCCUCCUCGCCCUCUUGCCCCCGGAGCCGCGAGCACCCAAG

SEQ ID NO:28

Figure 7C

Sequence of Her2 SMO Target Sequence 1

UGGGGCCGGAGCCGCAGUGAGCACCAUGGAGCUGGCGGCCUUGUGCCGCU    SEQ ID NO:29

Figure 7D

Sequence of Her2 SMO Target Sequence 2

CUUGCCCCAUCAACUGCACCCACUC    SEQ ID NO:30

Sequence of Her2 SMO Target Sequence 3

CCCUCUGACGUCCAUCAUCUCGGCG    SEQ ID NO:31

Prolactin Receptor - long form

Figure 8A

Sequence of Prolactin Receptor – long form precursor mRNA first 150 bp of exon 10 (capital letters
and 150 bp of flanking intron (small letters)

aaguguauucuagauggccuggcacacaaauguougaaguuugagaucuuccaccugcuuguggcaaugaacagcaccauuagcagg
gaugcugauuuggaauguuaugaagcuaacagccaucucuucuuguguougugunuuaauaGAAGGCAAGUCUGAAGAACUACUGAGU
GCCUUGGAUGCCAAGACUUCCUCCACUUCUGACUAUGAGGACUUCCUGGUGGAGUAUUUAGAAGUAGAUGAUAGUGAGGACCAGCA
UCUAAUGUCAGUCAUUCAAAAGAACACCCAAG

SEQ ID NO:32

Figure 8B

Sequence of Prolactin Receptor SMO Target Sequence 1

UGUGUCUGUGUUUUAAUAGAAGGGC    SEQ ID NO:33

Sequence of Prolactin Receptor SMO Target Sequence 2

CUUGAGUU    SEQ ID NO:34

Sequence of Prolactin Receptor SMO Target Sequence 3

CCCUCUAG    SEQ ID NO:35

Sequence of Prolactin Receptor SMO Target Sequence 4

GUACUGUUUUU    SEQ ID NO:36

Figure 8C

FIG. 8

SPLICE MODULATING OLIGONUCLEOTIDES THAT INHIBIT CANCER

REFERENCE TO SEQUENCE LISTING

A sequence listing is submitted herewith as an ASCII compliant text file with the file name "1279581SeqListing_ST25.txt", created on Nov. 15, 2013 and having a size of 11 kilobytes.

FIELD OF THE INVENTION

The invention relates to oligonucleotides that modify splicing, and their uses.

BACKGROUND

Related Art

Splicing is a post-transcriptional modification of precursor messenger RNA (pre-mRNA), in which introns thereof are removed and exons thereof are joined to form mature mRNA. For many eukaryotic introns, splicing is catalyzed by a spliceosome, a complex of small nuclear ribonucleoproteins (snRNPs) located in the nucleus. A 5' splice site, a 3' splice site, and a branch site are required for splicing an intron removed by a spliceosome. The 5' splice site, or splice donor site, occurs at the 5' end of the intron and includes an almost invariant GU sequence within a larger, less conserved consensus nucleotide sequence. The 3' splice site, or splice acceptor site, occurs at the 3' end of the intron and includes an almost invariant AG sequence downstream (3'-ward) from a region high in pyrimidines (C and U), or polypyrimidine tract. Upstream (5'-ward) from the polypyrimidine tract is the branch point, which includes an adenine nucleotide [1].

Two types of spliceosomes have been identified (major and minor), which contain different snRNPs. The major spliceosome is composed of U1, U2, U4, U5, and U6 snRNPs and splices introns that contain GU at the splice donor site and AG at the splice acceptor site. The minor spliceosome is composed of U4atac, U5, U6atac, U11, and U12 snRNPs and splices rare introns, which have specific splice donor and splice acceptor sequences, out of precursor mRNAs [2].

Alternative splicing is a phenomenon operative to create mature mRNA splice variants from pre-mRNA. Alternative splicing can occur in several ways: e.g., exons can be extended or skipped and/or introns can be retained. And mRNA splice variants may code for proteins that have related, distinct, or even opposing functions [3,4]. Alternative splicing can be regulated by cis-acting sequence motifs in pre-mRNAs referred to as exonic or intronic splice enhancers (ESEs or ISEs, respectively) and silencers (ESSs or ISSs, respectively), putatively recognized by non-spliceosomal, trans-acting factors. Splice enhancer and silencer motifs promote or suppress splice-site (ss) selection, respectively [5-7].

The prolactin receptor can be a target for breast cancer therapy. Up to 95% of primary breast tumors express the prolactin receptor compared to ~70% that express the estrogen receptor. Thus, therapies targeting the prolactin receptor can have greater utility than those targeting the estrogen receptor. Another feature of prolactin receptor targeting is that such therapy can target estrogen receptor negative tumors. Other reasons for choosing prolactin receptor targeting include: a) elevated serum prolactin levels are associated with an increased incidence of breast cancer equivalent to that seen with estrogen; b) prolactin receptors are expressed at higher levels in cancerous lesions versus normal tissue; c) high circulating prolactin is correlated with high breast density, itself associated with a higher incidence of breast cancer; d) most prolactin in the blood is produced by the pituitary, but breast cancer cells can also produce prolactin and use that prolactin to promote growth and survival; inhibiting the function of both pituitary and locally-produced prolactin can be accomplished by targeting the prolactin receptor; e) normal breast stem cells have been shown to express the prolactin receptor, thereby raising the possibility that breast cancer stem cells would also; targeting the cancer stem cells would eradicate all traces of the cancer [15-22].

Various forms of the prolactin receptor are produced by alternative splicing of prolactin pre-mRNA [23-25]. Of particular interest is a prolactin receptor long form that increases cancer cell survival and growth, and a prolactin receptor short form that decreases cell survival and cancer growth [26-28].

T helper cells (Th cells) are a sub-group of lymphocytes that play an important role in the adaptive immune system of a host. When mature Th cells express the cell surface glycoprotein CD4 molecule, they are called CD4+ T cells. These T cells help proper functioning of other immune cells, including the activation and growth of cytotoxic (CD8+) T cells (expressing cell surface glycoprotein CD8 molecule), to mount effective immunity against cancer and some kinds of infections. A central role in cancer immunity has been attributed to pro-inflammatory CD4+ effector T cells, and they have been duly recognized as critical determinants of an effective antitumor immune responses [8-11].

Interferon-γ (IFN-γ), a type II interferon, is one of the signature effector molecules secreted by tumor antigen-specific CD4 and CD8 effector T cells during the development of antitumor immunity and is effective in tumor control. IFN-γ in addition, has generalized immune-stimulatory and immune-modulatory effects in the immune system [12]. Another important aspect during antigen-specific immune responses, is the ability of responding T cells to produce Interleukin-2 (IL-2), which is necessary for the growth, proliferation, and differentiation of T cells to become "effector" T cells. The IL-2/IL-2(receptor)R interaction stimulates the growth, differentiation and survival of antigen-specific CD4+ T cells and CD8+ T cells and thus plays a critical role in the development of T cell immunologic memory [13].

SUMMARY

In one aspect, a method of treating cancer in a subject is provided. The method includes administering a splice modulating oligonucleotide to the subject in an amount effective to provide a therapeutic benefit to the subject. In the method, the oligonucleotide modifies splicing of a pre-mRNA encoding a polypeptide, and either: reduces expression of the polypeptide if the polypeptide promotes cancer cell survival, proliferation, and/or metastasis, or promotes angiogenesis, or a combination thereof; or increases expression of the polypeptide if the polypeptide inhibits cancer cell survival, proliferation and/or metastasis, or inhibits angiogenesis, or a combination thereof.

In the method:

a) The pre-mRNA can be a prolactin receptor pre-mRNA, growth hormone receptor pre-mRNA, insulin receptor premRNA, estrogen receptor α or β pre-mRNA, human epidermal growth factor receptor 2 (Her2) pre-mRNA, receptor tyrosine kinase ErbB4 pre-mRNA, or signal transducer and activator of transcription 5a (STAT5a) pre-mRNA.

b) The polypeptide can be prolactin receptor long form, a growth hormone receptor variant lacking part of exon 9, an insulin receptor variant lacking exon 11, an estrogen receptor α variant lacking exon 5 or exon 7, an estrogen receptor β variant lacking exon 5, a Her2 polypeptide variant lacking exon 16, an ErbB4 kinase variant lacking exon 26, or a STAT5a polypeptide variant lacking exon 5.

c) The amount is effective to increase apoptosis and/or necrosis of cancer cells; stimulate an anti-tumor T cell response, decrease Treg cell recruitment to a tumor associated with the cancer; decrease cancer stem cell numbers; or decrease cancer metastasis; or a combination thereof. In some embodiments, the anti-tumor T cell response comprises increasing tumor-specific CD4+ T cells, tumor-specific CD8+ T cells, or both, in the subject.

d) The oligonucleotide can be complementary to an intron/exon junction, a 5' splice site, a 3' splice site, a branch site, an intronic splice enhancer, or an exonic splice enhancer, of the pre-mRNA.

e) The cancer can be a cancer involving prolactin and/or the prolactin receptor. In particular embodiments, the cancer is breast cancer, prostate cancer or ovarian cancer. In particular embodiments, the pre-mRNA is prolactin receptor pre-mRNA, and the polypeptide is the prolactin receptor long form. In particular embodiments, the oligonucleotide has the following sequence: GCCCTTCTATTAAAACACAGACACA (SEQ ID NO:37) or GCCCTTCTATTGAAACACAGATACA (SEQ ID NO:38).

f) Or any combination of a)-e).

Any pre-mRNA consisting of 3 or more exons whose polypeptide product promotes the survival, proliferation or metastasis of cancer cells or tumor cells, or the process of angiogenesis, is contemplated. Alternatively, the pre-mRNA can be one where alteration of splicing will favor production of a dominant negative form of a polypeptide that inhibits the survival, proliferation or metastasis of cancer cells or tumor cells or the process of angiogenesis. Examples of polypeptides that promote survival, proliferation, metastasis or angiogenesis include, but are not limited to, the prolactin receptor long form, an insulin receptor variant lacking exon 11, an estrogen receptor α variant lacking exon 5, a Her2 polypeptide variant lacking exon 16, or a STAT5a polypeptide variant lacking exon 5. Examples of polypeptides that inhibit survival, proliferation metastasis or angiogenesis include, but are not limited to, a growth hormone receptor variant lacking part of exon 9, an estrogen receptor α variant lacking exon 7, an estrogen receptor β variant lacking exon 5, or an ErbB4 kinase variant lacking exon 26.

In another aspect, a method of treating breast cancer in a subject is provided. The method includes administering a splice modulating oligonucleotide of the following sequence to the subject in an amount effective to provide a therapeutic benefit: GCCCTTCTATTAAAACACAGACACA (SEQ ID NO:37) or GCCCTTCTATTGAAACACAGATACA (SEQ ID NO:38). In the method, the amount is effective to increase apoptosis and/or necrosis of the breast cancer cells; stimulate an anti-tumor T cell response, decrease Treg cell recruitment to a tumor containing the breast cancer cells; decrease breast cancer stem cell numbers; or decrease breast cancer metastasis; or any combination thereof. In some embodiments, the anti-tumor T cell response comprises increasing tumor-specific CD4+ T cells, tumor-specific CD8+ T cells, or both, in the subject.

In a further aspect, a method of treating a disease involving prolactin or the prolactin receptor is provided. The method includes administering a splice modulating oligonucleotide to the subject in an amount effective to provide a therapeutic benefit, where the oligonucleotide modifies splicing of the prolactin receptor pre-mRNA. In the method, the oligonucleotide can reduce the expression of the prolactin receptor long form; the oligonucleotide can have the following sequence: GCCCTTCTATTAAAACACAGACACA (SEQ ID NO:37) or GCCCTTCTATTGAAACACAGATACA (SEQ ID NO:38); the disease can be breast cancer, prostate cancer, ovarian cancer or lymphangioleiomyomatosis; or any combination thereof.

In another aspect, a splice modulating oligonucleotide of the following sequence is provided: GCCCTTCTATTAAAACACAGACACA (SEQ ID NO:37) or GCCCTTCTATTGAAACACAGATACA (SEQ ID NO:38).

In another aspect, a pharmaceutical composition is provided. The composition includes a splice modulating oligonucleotide having the following sequence: GCCCTTCTATTAAAACACAGACACA (SEQ ID NO:37) or GCCCTTCTATTGAAACACAGATACA (SEQ ID NO:38); and a pharmaceutically acceptable carrier.

In a further aspect, a method of stimulating T cell immunity is provided. The method includes exposing a subject to a splice modulating oligonucleotide in an amount sufficient to inhibit expression of a target protein. In the method: the target protein can be the prolactin receptor long form; the splice modulating oligonucleotide can modulate splicing of the prolactin receptor long form precursor mRNA; the splice modulating oligonucleotide can inhibit expression of the prolactin receptor long form mRNA; stimulating T cell immunity can include stimulating anti-tumor T cell immunity; the stimulating can include increasing the levels of CD4+ T cells, CD8+ T cells, or both, in the subject; the CD4+ T cells, CD8+ T cells, or both, can be anti-tumor effector T cells; or any combination thereof.

In any method, the subject can be a human or other animal, such as a mouse.

Examples of cancers include cancers of the bladder, blood, bone, bone marrow, brain, breast, colon, esophagus, gastrointestine, gums, head, kidney, liver, lung, nasopharynx, neck, ovary, prostate, skin, stomach, testis, tongue, or uterus. In some embodiments of the invention, the compositions and methods can be used in the context of hyperproliferative diseases, or in the context of angiogenesis or diseases involving angiogenesis, such as some hyperproliferative diseases including cancer.

In a further aspect, a method of modulating splicing of a precursor mRNA (pre-mRNA) present in a cell is provided. The method includes exposing the cell to an effective amount of a splice modulating oligonucleotide (SMO), wherein: the SMO comprises a single-stranded sequence, at least eight nucleotides in length, configured to facilitate SMO hybridization to a target nucleotide sequence in the pre-mRNA that comprises or overlaps at least one of an intron-exon junction, a 5' splice site, a 3' splice site, a branch site, and a splice enhancer element; and SMO hybridization to the target sequence inhibits splicing an exon, in the pre-mRNA, into a mature mRNA produced from the pre-mRNA.

In the method, the exon can be selected from: a) the group consisting of an estrogen receptor α exon 7, an estrogen receptor β exon 5, an ErbB4 exon 26, a PRLR exon 10, a growth hormone receptor exon 9 partial; b) the estrogen receptor α exon 7, and wherein the target sequence appears in FIG. 1D; c) the estrogen receptor β exon 5, and wherein the target sequence appears in FIG. 2C; d) the ErbB4 exon 26, and wherein the target sequence appears in at least one of FIG. 5B and FIG. 5C; e) the PRLR exon 10, and wherein the target sequence appears in FIG. 8C Prolactin Receptor SMO Target Sequence 1; f) the growth hormone receptor exon 9 partial, and wherein the target sequence appears in FIG. 4D Growth Hormone Receptor SMO Target Sequence 1.

In another aspect, a method of modulating splicing of a pre-mRNA present in a cell is provided. The method includes exposing the cell to an effective amount of a SMO, wherein: the SMO comprises a single-stranded sequence, at least eight nucleotides in length, configured to facilitate SMO hybridization to a target nucleotide sequence in the pre-mRNA that comprises or overlaps a splice silencer element; and SMO hybridization to the target sequence promotes splicing an exon, in the pre-mRNA, into a mature mRNA produced from the pre-mRNA. In the method, exon can be exon 11 of prolactin receptor pre-mRNA, and wherein the target sequence appears in at least one of FIG. 8C Prolactin Receptor SMO Target Sequence 2, 3, and 4.

In a further aspect, a method of decreasing an amount of a protein present in a cell is provided. The method includes exposing the cell to an effective amount of a SMO, wherein: the SMO comprises one or more single-stranded sequence(s), at least eight nucleotides in length, configured to facilitate SMO hybridization to one or more target nucleotide sequence(s) in the pre-mRNA that comprise(s) or overlap(s) a first nucleotide sequence or second and third nucleotide sequences; the first nucleotide sequence resides in an exon of the pre-mRNA; the second and third nucleotide sequences reside in two different exons of the pre-mRNA, and SMO hybridization to the one or more target sequence(s): (i) inhibits translation of a mature mRNA that is produced from the pre-mRNA and that codes for the protein, (ii) promotes degradation of the pre-mRNA and thereby inhibits production of the mature mRNA; or (iii) both (i) and (i).

In the method, the first nucleotide sequence can reside in: a) exon 1 of Her2 pre-mRNA or an exon 7 of estrogen receptor α pre-mRNA; b) exon 1 of Her2 pre-mRNA and appears in FIG. 7D; c) exon 7 of estrogen receptor α pre-mRNA and appears in FIG. 1A. In the method, the second and third nucleotide sequences can reside in: a) exon 15 and exon 17 of Her2 pre-mRNA; b) exon 4 and exon 6 of STAT5a pre-mRNA; c) exon 10 and exon 12 of insulin receptor pre-mRNA; d) exon 15 and the exon 17 of Her2 pre-mRNA and appear in FIG. 7E Her2 SMO Target Sequence 2 and 3, respectively; e) exon 4 and exon 6 of STAT5a pre-mRNA and appear in FIG. 3C STAT5a SMO Target Sequence 1 and 2, respectively; f) exon 10 and the exon 12 of insulin receptor pre-mRNA and appear in FIG. 6C Insulin Receptor SMO Target Sequence 1 and 2, respectively.

In a further aspect, an SMO for modulating splicing of a pre-mRNA present in a cell is provided. The SMO includes a single-stranded sequence, at least eight nucleotides in length, configured to facilitate SMO hybridization to a target nucleotide sequence in the pre-mRNA that comprises or overlaps at least one of an intron-exon junction, a 5' splice site, a 3' splice site, a branch site, and a splice enhancer element, wherein: SMO hybridization to the target sequence inhibits splicing an exon, in the pre-mRNA, into a mature mRNA produced from the pre-mRNA.

In the SMO, the exon can be: a) an estrogen receptor α exon 7, an estrogen receptor β exon 5, an ErbB4 exon 26, a PRLR exon 10, or a growth hormone receptor exon 9 partial; b) the estrogen receptor α exon 7, and wherein the target sequence appears in FIG. 1D; c) the estrogen receptor β exon 5, and wherein the target sequence appears in FIG. 2C; d) the ErbB4 exon 26, and wherein the target sequence appears in at least one of FIG. 5B and FIG. 5C; e) the PRLR exon 10, and wherein the target sequence appears in FIG. 8C Prolactin Receptor SMO Target Sequence 1; f) the growth hormone receptor exon 9 partial, and wherein the target sequence appears in FIG. 4B Growth Hormone Receptor SMO Target Sequence 1.

In another aspect, an SMO, for modulating splicing of a pre-mRNA present in a cell is provided. The SMO includes a single-stranded sequence, at least eight nucleotides in length, configured to facilitate SMO hybridization to a target nucleotide sequence in the pre-mRNA that comprises or overlaps a splice silencer element, wherein: SMO hybridization to the target sequence promotes splicing an exon, in the pre-mRNA, into a mature mRNA produced from the pre-mRNA. In the SMO, the exon can be exon 11 of prolactin receptor pre-mRNA and wherein the target sequence appears in at least one of FIG. 8C Prolactin Receptor SMO Target Sequence 2, 3, and 4.

In a further aspect, an SMO for decreasing an amount of a protein present in a cell is provided. The SMO includes one or more single-stranded sequence(s), at least eight nucleotides in length, configured to facilitate SMO hybridization to one or more target nucleotide sequence(s) in the pre-mRNA that comprise(s) or overlap(s) a first nucleotide sequence or second and third nucleotide sequences; the first nucleotide sequence resides in an exon of the pre-mRNA; the second and third nucleotide sequences reside in two different exons of the pre-mRNA; and SMO hybridization to the one or more target sequence(s): (i) inhibits translation of a mature mRNA that is produced from the pre-mRNA and that codes for the protein, (ii) promotes degradation of the pre-mRNA and thereby inhibits production of the mature mRNA; or (iii) both (i) and (ii).

In the SMO, the first nucleotide sequence can reside in: a) exon 1 of Her2 pre-mRNA or exon 7 of estrogen receptor α pre-mRNA; b) exon 1 of Her2 pre-mRNA and appears in FIG. 7D; c) exon 7 of estrogen receptor α pre-mRNA and appears in FIG. 1A. In the SMO, the second and third nucleotide sequences can reside in: a) exon 15 and an exon 17 of Her2 pre-mRNA; b) exon 4 and exon 6 of STAT5a pre-mRNA; c) exon 10 and exon 12 of insulin receptor pre-mRNA; d) exon 15 and exon 17 of Her2 pre-mRNA; e) exon 4 and exon 6 of STAT5a pre-mRNA; f) exon 10 and exon 12 of insulin receptor pre-mRNA; g) exon 15 and the exon 17 of Her2 pre-mRNA and appear in FIG. 7E Her2 SMO Target Sequence 2 and 3, respectively; h) exon 4 and exon 6 of STAT5a pre-mRNA and appear in FIG. 3C STAT5a SMO Target Sequence 1 and 2, respectively; i) exon 10 and exon 12 of insulin receptor pre-mRNA and appear in FIG. 6C insulin receptor SMO Target Sequence 1 and 2, respectively.

BRIEF DESCRIPTION OF THE DRAWINGS

For a more complete understanding of the present invention, reference is now made to the accompanying drawings, in which:

FIGS. 1A-1D illustrate the intron-exon structure of human estrogen receptor α pre-mRNA (FIG. 1A); the nucleotide sequence for exons 5 and 7 of the human estrogen receptor α pre-mRNA plus 150 nucleotides of flanking intron sequence (FIGS. 1B and 1C, respectively); and the nucleotide sequences of human estrogen receptor α premRNA SMO target sequences 1-4 (FIG. 1D), 5' end on left and 3' end on right for all. FIG. 1A shows that the intron-exon structure of the human estrogen receptor α pre-mRNA includes eight exons (rectangles labeled 1-8) separated by introns (slanted lines). The scale bar at the upper right of FIG. 1A represents 100 kilobases.

FIGS. 2A-2C illustrate the intron-exon structure of human estrogen receptor β pre-mRNA (FIG. 2A); the nucleotide sequence for exon 5 of the human estrogen receptor β pre-mRNA plus 150 nucleotides of flanking intron sequence (FIG. 2B); and the nucleotide sequences of human estrogen receptor β pre-mRNA SMO target sequences 1-4 (FIG. 2C), 5' end on left and 3' end on right for all. FIG. 2A shows that the intron-exon structure of the human estrogen receptor β pre-mRNA includes nine exons (rectangles labeled 1-9) separated by introns (slanted lines). The scale bar at the upper right of FIG. 2A represents 100 kilobases.

FIGS. 3A-3C illustrate the intron-exon structure of human STAT5a pre-mRNA (FIG. 3A); the nucleotide sequence for exon 5 of the human STAT5a pre-mRNA plus 150 nucleotides of flanking intron sequence (FIG. 3B); and the nucleotide sequences of STAT5a pre-mRNA SMO target sequences 1 and 2 (FIG. 3C), 5' end on left and 3' end on right for all. FIG. 3A shows that the intron-exon structure of the human STAT5a pre-mRNA includes 20 exons (rectangles labeled 1-20) separated by introns (slanted lines). The scale bar at the upper right of FIG. 3A represents 1 kilobase.

FIGS. 4A-4D illustrate the intron-exon structure of human growth hormone receptor pre-mRNA (FIG. 4A); the nucleotide sequence for exons 8 and 9 of the human growth hormone receptor pre-mRNA plus 150 nucleotides of flanking intron sequence (FIGS. 4B and 4C, respectively); and the nucleotide sequences of human growth hormone receptor α pre-mRNA SMO target sequences 1-3 (FIG. 4D), 5' end on left and 3' end on right for all. FIG. 4A shows that the intron-exon structure of the human growth hormone receptor pre-mRNA includes 10 exons (rectangles labeled 1-10) separated by introns (slanted lines). The scale bar at the upper right of FIG. 4A represents 10 kilobases.

FIGS. 5A-5C illustrate the intron-exon structure of human ErbB4 pre-mRNA (FIG. 5A); the nucleotide sequence for exon 26 of the human ErbB4 pre-mRNA plus 150 nucleotides of flanking intron sequence (FIG. 5B); and the nucleotide sequences of ErbB4 pre-mRNA SMO target sequences 1-7 (FIG. 5C), 5' end on left and 3' end on right for all. FIG. 5A shows that the intron-exon structure of the human ErbB4 pre-mRNA includes 28 exons (rectangles labeled 1-28) separated by introns (slanted lines). The scale bar at the upper right of FIG. 5A represents 100 kilobases.

FIGS. 6A-6C illustrate the intron-exon structure of human insulin receptor pre-mRNA (FIG. 6A); the nucleotide sequence for exon 11 of the human insulin receptor pre-mRNA plus 150 nucleotides of flanking intron sequence (FIG. 6B); and the nucleotide sequences of human insulin receptor SMO pre-mRNA target sequences 1 and 2 (FIG. 6C), 5' end on left and 3' end on right for all. FIG. 6A shows that the intron-exon structure of the human insulin receptor pre-mRNA includes 22 exons (rectangles labeled 1-22) separated by introns (slanted lines). The scale bar at the upper right of FIG. 6A represents 10 kilobases.

FIGS. 7A-7E illustrate the intron-exon structure of human Her2 pre-mRNA (FIG. 7A); the nucleotide sequence for exons 16 and 1 of the human Her2 pre-mRNA plus 150 nucleotides of flanking intron sequence (FIGS. 7B and 7C, respectively); and the nucleotide sequence of human Her2 pre-mRNA SMO target sequences 1-3 (FIGS. 7D and 7E), 5' end on left and 3' end on right for all. FIG. 7A shows that the intron-exon structure of the human growth.

FIGS. 8A-8C illustrate the intron-exon structure of human prolactin receptor-long form pre-mRNA (FIG. 8A); the nucleotide sequence for exon 10 of the human prolactin receptor-long form pre-mRNA plus 150 nucleotides of flanking intron sequence (FIG. 8B); and the nucleotide sequences of human prolactin receptor-long form pre-mRNA SMO target sequences 1-4 (FIG. 8C), 5' end on left and 3' end on right for all. FIG. 8A shows that the intron-exon structure of the human prolactin receptor-long form pre-mRNA includes 10 exons (rectangles labeled 1-10) separated by introns (slanted lines). The scale bar at the upper right of FIG. 8A represents 10 kilobases.

DETAILED DESCRIPTION

Figure 9:
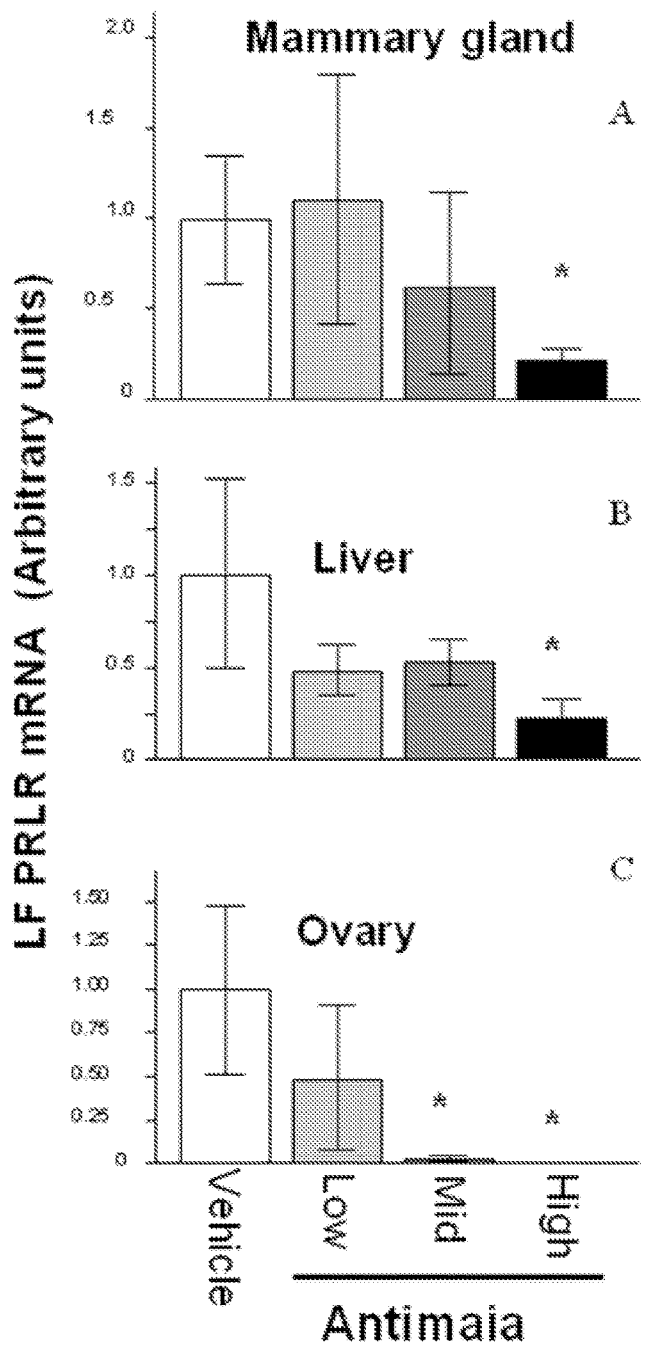
FIGS. 9A-9C show expression levels of the long form (LF) of the prolactin receptor in mammary gland, liver and ovary.
Figure 10:
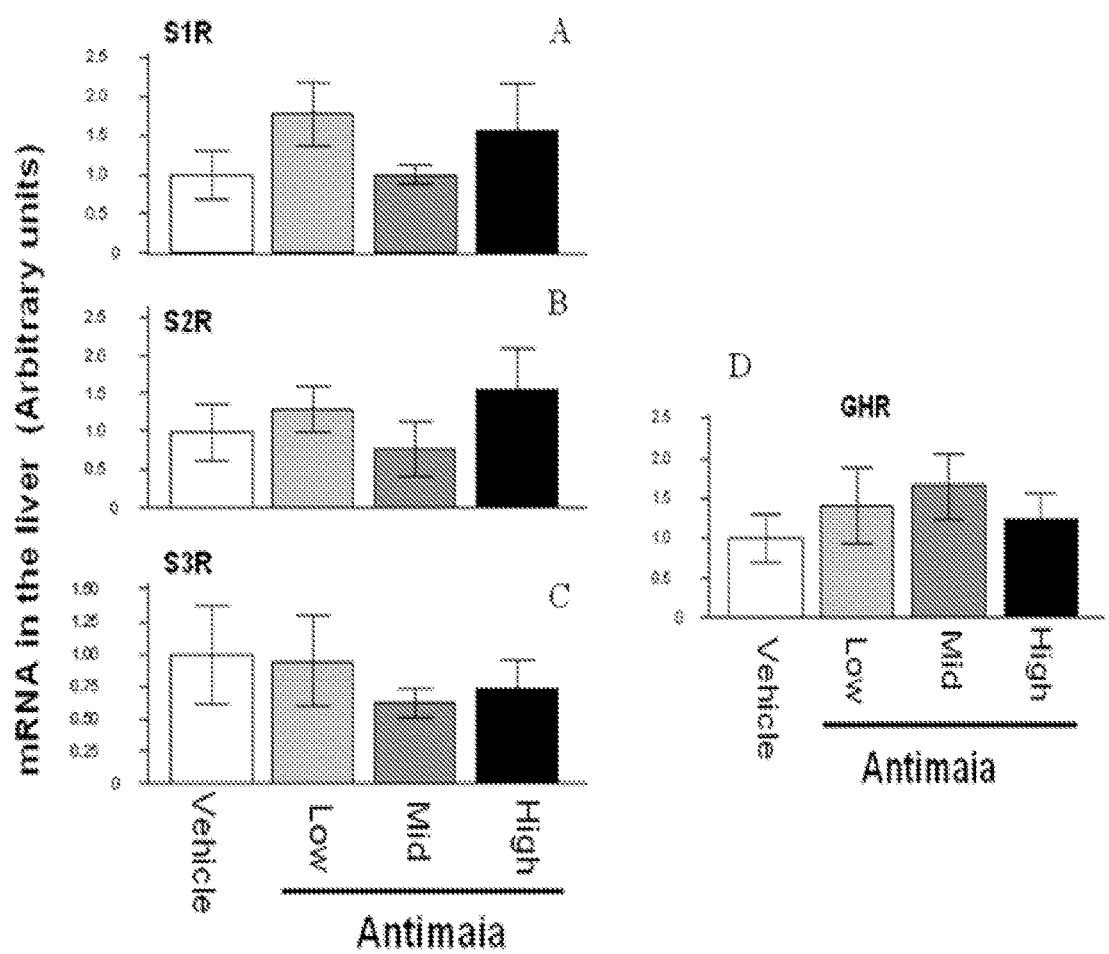
FIGS. 10A-10D show expression levels of short prolactin receptor forms (10A-10C), and the growth hormone receptor (10D).

The following applications are incorporated by reference herein: Provisional Patent Application No. 61/727,030, filed on Nov. 15, 2012.

Alternative splicing of pre-mRNA can lead to the production of mature mRNAs that code for different forms of a protein, including wild-type, constitutively active, or dominant negative forms, by either inclusion or exclusion of particular exons in mature mRNAs. A variety of mammalian conditions and diseases, including certain types of cancer, arise and/or progress from mis-expression of wild-type, constitutively-active, or dominant negative forms of proteins (e.g., ligands, receptors, kinases, and transcription factors). Techniques and compositions useful for selectively modulating the production, from pre-mRNA, of mature mRNA or the translation thereof that codes for wild-type, constitutively active, and/or dominant negative forms of protein would have application in, e.g., inhibiting incidence or progression of mammalian disease, such as certain types of cancer.

Certain embodiments of the invention provide methods of modulating the splicing of a pre-mRNA present in a cell of a mammal. In some embodiments, such methods involve bringing the cell into contact with an effective amount of a splice modulating oligonucleotide (SMO). In some embodiments, the SMO is characterized by having a single-stranded sequence, at least eight nucleotides in length, that facilitates SMO hybridization to a target sequence in the pre-mRNA that comprises or overlaps at least one of an intron-exon junction, a 5' splice site, a 3' splice site, a branch site, an intronic splice enhancer, and an exonic splice enhancer. And SMO hybridization to the target sequence inhibits splicing an exon, in the pre-mRNA, into a mature mRNA, produced from the pre-mRNA, that codes for a protein, expression of which in the cell of the mammal inhibits an incidence or a progression of a cancer in the mammal.

Certain embodiments of the invention provide methods of modulating the splicing of a pre-mRNA present in a cell of a mammal. In some embodiments, such methods involve bringing the cell into contact with an effective amount of a SMO. In some embodiments, the SMO is characterized by having a single-stranded sequence, at least eight nucleotides in length, that facilitates SMO hybridization to a target sequence in the pre-mRNA that comprises or overlaps at least one of an intronic splice silencer and an exonic splice silencer. And SMO hybridization to the target sequence promotes splicing of an exon, which resides in the pre-mRNA, into a first mature mRNA that codes for a protein, expression of which in the cell inhibits an incidence or a progression of a cancer in the mammal.

Certain embodiments of the invention provide SMOs for modulating splicing of a pre-mRNA present in a cell of a mammal. In such embodiments, SMOs can be characterized by having a single-stranded sequence, at least eight nucleotides in length, configured to facilitate SMO hybridization to a target sequence in the pre-mRNA that comprises or overlaps at least one of an intron-exon junction, a 5' splice site, a 3' splice site, a branch site, an intronic splice enhancer, and an exonic splice enhancer. And SMO hybridization to the target sequence inhibits splicing an exon, in the pre-mRNA, into a mature mRNA, produced from the pre-mRNA, that codes for a protein, expression of which in the cell of the mammal inhibits an incidence or a progression of a cancer in the mammal Certain embodiments of the invention provide SMOs for modulating splicing of a pre-mRNA present in a cell of a mammal. In such embodiments, SMOs can be characterized by having a single-stranded sequence, at least eight nucleotides in length, configured to facilitate SMO hybridization to a target sequence in the pre-mRNA that comprises or overlaps at least one of an intronic splice silencer and an exonic splice silencer. And SMO hybridization to the target sequence promotes splicing of an exon, in the pre-mRNA, into a first mature mRNA that codes for a protein, expression of which in the cell inhibits an incidence or a progression of a cancer in the mammal.

Certain embodiments of the invention provide methods of decreasing an amount of a protein present in a cell of a mammal, comprising exposing the cell to an effective amount of a SMO, in which the SMO comprises a single-stranded sequence, at least eight nucleotides in length, configured to facilitate SMO hybridization to one or more target nucleotide sequence(s) in the pre-mRNA that comprise(s) or overlap(s) a first nucleotide sequence or second and third nucleotide sequences; the first nucleotide sequence resides in an exon of the pre-mRNA; the second and third nucleotide sequences reside in two different exons of the pre-mRNA; SMO hybridization to the one or more target sequence(s): (i) inhibits translation of a mature mRNA produced from the pre-mRNA, (ii) promotes degradation of the pre-mRNA and thereby inhibits production of the mature mRNA; or (iii) both (i) and (ii); and the mature mRNA codes for a protein, expression of which in the cell is associated with an incidence or a progression of a cancer in the mammal.

Certain embodiments of the invention provide a SMO, for increasing a degradation rate of a pre-mRNA present in a cell of a mammal, that comprises a single-stranded sequence, at least eight nucleotides in length, configured to facilitate SMO hybridization to one or more target sequence(s) in the pre-mRNA that comprise(s) or overlap(s) a first nucleotide sequence or second and third nucleotide sequences, in which the first nucleotide sequence resides in an exon of the pre-mRNA; the second and third nucleotide sequences reside in two different exons of the pre-mRNA; and SMO hybridization to the one or more target sequence(s) promotes degradation of the pre-mRNA and inhibits production of a mature mRNA from the pre-mRNA that codes for a protein, expression of which in the cell is associated with an incidence or a progression of a cancer in the mammal.

As used herein, the term, "splice modulating oligonucleotide" refers to an oligonucleotide, 7-100 nucleotides in lengths, characterized by having a nucleotide sequence that is complementary to a target nucleotide sequence in a pre-mRNA present in a mammalian cell and renders the oligonucleotide operative, when contacted with the mammalian cell in therapeutically effective amounts, to modulate (e.g., up-regulate or down-regulate) an amount of a mRNA splice variant produced from the pre-mRNA in the cell or to increase a degradation rate of the pre-mRNA in the cell and/or decrease a translation rate of a mRNA. In embodiments in which SMOs modulate splicing of a pre-mRNA, such SMOs may comprise a nucleotide sequence complementary to a target sequence in the pre-mRNA that comprises or overlaps: an intron-exon junction; an intronic splice silencer; and/or an intronic splice enhancer. In embodiments in which SMOs increase a pre-mRNA degradation rate or decrease a mRNA translation rate, such SMOs may comprise a nucleotide sequence complementary to one or more target sequence(s) in the pre-mRNA that comprise(s) or overlap(s) a nucleotide sequence from a single exon or two or more nucleotide sequences from two or more exons.

The nucleotides of SMOs can be modified or unmodified DNA nucleotides, RNA nucleotides, or combinations thereof. In some embodiments, an SMO composition comprises at least one of a DNA oligonucleotide, an RNA oligonucleotide, a morpholino, or a "vivo morpholino". In particular, the oligonucleotide can include modified oligonucleotide backbones such as, but not limited to, phosphorothioates, chiral phosphorothioates, phosphorodithioates, phosphotriesters, aminoalkylphosphotriesters, methyl and other alkyl phosphonates 3'-alkylene phosphonates and chiral phosphonates), phosphinates, phosphoramidates 3'-amino phosphoramidate and aminoalkylphosphoramidates), thionophosphoramidates, thionoalkylphosphonates, thionoalkyl phosphotriesters, and boranophosphates having normal 3'-5' linkages, as well as 2'-5' linked analogs of these, and those having inverted polarity wherein the adjacent pairs of nucleoside units are linked 3'-5' to 5'-3' or 2'-5' to Various salts, mixed salts and free acid forms are also included. References that teach the preparation of such modified backbone oligonucleotides are provided, for example, in U.S. Pat. Nos. 4,469,863 and 5,750,666, all incorporated by reference herein [29, 30]. The design and synthesis of antisense oligonucleotides is well known in the art [31]. Computer programs for the design of antisense oligonucleotide sequences are also available [32].

In some embodiments, at least seven, eight, 10, 15, 20, 25, 30, 40, or 50 contiguous nucleotides in a SMO are complementary to the target nucleotide sequence in the selected pre-mRNA that comprises, or overlaps, a sequence motif selected from the group consisting of a 5' splice site, a 3' splice site, a branch site, an intronic splice enhancer, an intronic splice silencer, an exonic splice enhancer, and an exonic splice silencer. In some embodiments, at 8-12, 8-15, 8-20, 10-25, 15-30, 20-40, or 30-50 contiguous nucleotides in a SMO are complementary to the target nucleotide sequence in the selected pre-mRNA that comprises, or overlaps, a sequence motif selected from the group consisting of a 5' splice site, a 3' splice site, a branch site, an intronic splice enhancer, an intronic splice silencer, an exonic splice enhancer, and an exonic splice silencer.

In some embodiments, an SMO is 7-50 nucleotides in length, 7-25 nucleotides in length, 7-15 nucleotides in length, 8-12 nucleotides in length, 8-17 nucleotides in length, 8-25 nucleotides in length, 8-50 nucleotides in length, 9-12 nucleotides in length, 9-25 nucleotides in length, 10-17 nucleotides in length, 10-25 nucleotides in length, 20-30 nucleotides in length, or 25 nucleotides in length. In embodiments where an SMO comprises at least 75% RNA nucleotides, the SMO can be less than 21 nucleotides in length. In some embodiments, an SMO is entirely single-stranded. In some embodiments, an SMO is partially single-stranded. In some embodiments, an SMO is capable of reversibly or permanently forming stem loop structures, hairpin structures, and the like.

As used herein, the term "complementary" is used to in reference oligonucleotide sequences capable of base pairing to form a double-stranded nucleic acid molecule, under conditions selected from physiologic, high stringency, medium stringency, and low stringency. As used herein, the terms "hybridize" and "hybridization" refer to single stranded nucleic acid molecules base pairing with one another to form a double-stranded helix molecule, the nucleic acid molecules characterized by being complementary, either exactly or to a high percentage, such as 70%, 75%, 80%, 85%, 90%, 95%, 96%, 97%, 98%, 99%, and 100%.

Hybridization stringency is a function of probe length, probe composition (G+C content), salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C.

The relationship of hybridization conditions to Tm (in ° C.) is expressed in the mathematical equations: $T_m=81.5-16.6(\log 10[Na+])+0.41(\% G+C)-(600/N)$ (Equ. 1), where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide). $Tm=81.5+16.6 \log([Na+]/(1+0.7[Na+])+0.41(\% G+C)-500/L\ 0.63(\% \text{formamide})$ (Equ. 2), where L is the length of the probe in the hybrid [14]. The $T_m$ of equation (2) is affected by the nature of the hybrid; for DNA-RNA hybrids $T_m$ is 10-15° C. higher than calculated, for RNA-RNA hybrids Tm is 20-25° C. higher. Because the Tm decreases about 1° C. for each 1% decrease in homology when a long probe is used (see, Bonner et al., J. Mol. Biol. 81:123 (1973)), stringency conditions can be adjusted to favor detection of identical genes or related family members. Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below Tm, medium or moderate stringency is 26-29° C. below Tm and low stringency is 45-48° C. below Tm.

As used herein, the term "intron-exon junction" refers to sequences of nucleotides in a pre-mRNA that reside at the junction of an intron and an exon in the pre-mRNA. An intron-exon junction may extend up to 4 nucleotides, 5 nucleotides, 6 nucleotides, 7 nucleotides, 8 nucleotides, 9 nucleotides, 10 nucleotides, 15 nucleotides, 20 nucleotides, 25 nucleotides, 30 nucleotides, 35 nucleotides, 40 nucleotides, 45 nucleotides, and 50 nucleotides in both 5 '-ward and 3'-ward directions from the intron-exon border.

Methods for introducing SMOs of the invention into the body of a mammal (e.g., a human or mouse) in need thereof include any route of administration effective to enable the SMOs to perform their intended function, non-limiting examples of which are orally, intranasally, parenterally (intravenously, intramuscularly, intraperitoneally, or subcutaneously), intratumorally (including by one or more intratumoral injections), rectally, via an implant, an implanted pump, and topically. Amounts of SMOs of the invention administered to a mammal (e.g., a human) include any amount effective to enable the SMOs to perform their intended function. The amount of active compound to be administered to the patient varies according to the weight of the patient, the mode of administration, the indication and the severity of the disease. The clinician will be well suited to make such decisions based on the efficacy and toxicity (if any) of the therapeutic formulations.

Implantable drug delivery devices, also referred to as implanted pumps or drug delivery pumps, can be used to administer therapeutic agents to various locations within the body. Some drug delivery devices have variable volumetric flow rates, adjustable through an external programmer device. Other implantable drug delivery devices have fixed volumetric flow rates, but can be activated and deactivated externally. Still other drug delivery devices have fixed volumetric flow rates and are not adapted to be controlled from outside of the body. For example, implantable, electromechanical drug delivery devices can include, within a fluid impermeable and sealed casing, a watch-type drive mechanism that drives a circular wheel. Microchip based drug delivery devices are also available, and can include a plurality of drug reservoirs etched into a substrate to produce, for example, a single microchip.

Embodiments including a pharmaceutical composition will typically contain a pharmaceutically acceptable carrier. Depending on the intended mode of administration, the pharmaceutical composition may be in the form of solid, semi-solid or liquid dosage forms, such as, for example, tablets, suppositories, pills, capsules, powders, liquids, suspensions, ointments or lotions. A carrier can be any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. preferably in unit dosage form suitable for single administration of a precise dosage. One skilled in the art may formulate the compound in an appropriate manner, and in accordance with accepted practices, such as those disclosed in Remington's Pharmaceutical Sciences, Gennaro, Ed., Mack Publishing Co., Easton, Pa. 1990.

To determine the effects on splicing in vivo, pumps can be implanted into mice that administered thereto 1 μl/hr of one of the following four solutions. A solution that contains 100 μM of a SMO that targets mouse PRLR-long form (High), a solution that contains 10 μM of the SMO (Mid), a solution that contained 1 μM of the SMO (Low), or a control PBS solution that contains no SMO (PBS). Five days after pump implantation, expression levels of mouse PRLR-long form mRNA, mouse PRLR-short form S2 mRNA, and GAPDH mRNA can be assayed, for example, in liver tissue, ovary and mammary gland tissue. Expression levels of mouse PRLR-long form mRNA and mouse PRLR-short form S2 mRNA can be normalized to GAPDH in corresponding tissue samples, and reported in arbitrary units on the Y axes of graphs.

In other assays, a solution can contain, for example, 100 μM of a SMO that targets mouse PRLR-long form, a solution that contains 100 μM control oligomer, or a control PBS solution that contains no SMO (PBS). Five days after pump implantation, expression levels of mouse PRLR-long form mRNA, mouse PRLR-short form S2 mRNA, and GAPDH mRNA can be assayed in liver tissue, ovary tissue or mammary gland tissue. Expression levels of mouse PRLR-long form mRNA and mouse PRLR-short form S2 mRNA can be normalized to GAPDH in corresponding tissue samples, and reported in arbitrary units on the Y axes of graphs.

The terms "treatment" and "to treat" refer to providing therapeutic benefit including anything that promotes or enhances the well-being of the subject with respect to the medical treatment of his condition. A list of nonexhaustive examples of this therapeutic benefit includes extension of the subject's life by any period of time, a decrease in pain to the subject that can be attributed to the subject's condition, a decrease in the severity of the disease, an increase in the therapeutic effect of a therapeutic agent, an improvement in the prognosis of the condition or disease, a decrease in the amount or frequency of administration of a therapeutic agent, an alteration in the treatment regimen of the subject that reduces invasiveness of treatment, a decrease in the number of normal (non-cancerous) cells undergoing apoptosis so as to reduce injury to a tissue, an increase in the number of cells undergoing apoptosis when hyperproliferation is at least partially responsible for a condition or disease, and a decrease in the severity or frequency of side effects from a therapeutic agent. With respect to the treatment of cancer, therapeutic benefits also include a decrease or delay in the neoplastic development of the disease, decrease in hyperproliferation, reduction in tumor growth, delay or reduction of metastases, reduction of cancer stem cell number, and reduction in cancer cell or tumor cell proliferation rate.

Pertinent to certain embodiments of the invention, a wild-type form of human estrogen receptor α (ERα) protein is encoded by mRNA comprised of exons 1-8 of ERα pre-mRNA (FIG. 1A) spliced together. And splice variants produced from the ERα pre-mRNA code for constitutively active and dominant negative forms of ERα protein. A Δ5ERα splice variant: comprises exons 1-4 and 6-8 of the ERα pre-mRNA (FIG. 1A) spliced together, and codes for a constitutively active form of ERα protein. A Δ7ERα splice variant: comprises exons 1-6 and 8 of the ERα pre-mRNA (FIG. 1A) spliced together; and codes for another dominant negative form of ERα protein. In some embodiments of the invention, Δ5ERα mRNA can be advantageously modulated in a mammalian (e.g., a human or mouse) cell using SMOs. In some embodiments of the invention, Δ7ERα mRNA can be advantageously modulated in a mammalian (e.g., a human or mouse) cell using SMOs.

Pertinent to certain embodiments of the invention, a wild-type form of human estrogen receptor β (ERβ) protein is encoded by mRNA comprised of exons 1-9 of ERβ pre-mRNA (FIG. 2A) spliced together. And a splice variant produced from ERβ pre-mRNA codes for a dominant negative form of ERβ protein, Δ5ERβ, which comprises exons 1-4 and 6-9 of the ERα pre-mRNA (FIG. 2A) spliced together. In some embodiments of the invention, Δ5ERβ mRNA can be advantageously modulated in a mammalian (e.g., a human or mouse) cell using SMOs.

Pertinent to certain embodiments of the invention, a wild-type form of human signal transducer and activator of transcription 5a (STAT5a) protein is encoded by mRNA comprised of exons 1-20 of STAT5a pre-mRNA (FIG. 3A) spliced together. A Δ5STAT5a splice variant that comprises exons 1-4 and 6-20 is expressed in certain cancers. In some embodiments of the invention, the expression of Δ5STAT5a splice variant mRNA can be advantageously modulated in a mammalian (e.g., a mouse or human) cell using SMOs.

Pertinent to certain embodiments of the invention, a wild-type form of human growth hormone receptor (GHR) protein is encoded by mRNA comprised of exons 1-10 of GHR pre-mRNA (FIG. 4A) spliced together. And a PΔ9GHR splice variant: (i) comprises exons 1-8 and part of exon 9 of the GHR pre-mRNA (FIG. 4A) spliced together, and (ii) codes for a dominant negative form of GHR protein. In some embodiments of the invention, PΔ9GHR mRNA can be advantageously modulated in a mammalian (e.g., a mouse or human) cell using SMOs.

Pertinent to certain embodiments of the invention, a wild-type form of ErbB4 protein is encoded by mRNA comprised of exons 1-28 of ErbB4 pre-mRNA (FIG. 5A) spliced together. And a Δ26ErbB4 splice variant: (i) comprises exons 1-25 and 27-28 of ErbB4 pre-mRNA (FIG. 5A) spliced together; and (ii) codes for a dominant negative form of ErbB4 protein. In some embodiments of the invention, Δ26ErbB4 mRNA can be advantageously modulated in a mammalian (e.g., a mouse or human) cell using SMOs.

Pertinent to certain embodiments of the invention, a wild-type form of a human insulin receptor (IR) protein is encoded by mRNA comprised of exons 1-22 of IR pre-mRNA (FIG. 6A) spliced together. And a Δ11IR splice variant: (i) comprises exons 1-10 and 12-22 of IR pre-mRNA (FIG. 6A) spliced together; and (ii) codes for a form of IR protein found in cancer. In some embodiments of the invention, the expression Δ11IR mRNA can be advantageously modulated in a mammalian (e.g., a mouse or human) cell using SMOs in a variety of contexts.

Pertinent to certain embodiments of the invention, a wild-type form of Her2 protein is encoded by mRNA comprised of exons 1-27 of Her2 pre-mRNA (FIG. 7A) spliced together. And a Δ16Her2 splice variant: comprises exons 1-15 and 17-27 of Her2 pre-mRNA (FIG. 7A) spliced together, and codes for a constitutively active form of Her2 protein.

In some embodiments of the invention, the expression of Δ16Her2 mRNA can be advantageously down-regulated in a mammalian (e.g., a mouse or human) cell using SMOs. For example, overexpression of wild-type Her2 is found in aggressive breast and gastric cancers characterized by poor prognosis for time to progression and survival. The Δ16Her2 mRNA codes for a protein that has a small deletion in the extracellular domain of wild-type Her2 protein. The deletion removes some extracellular cysteine residues, leaving some remaining extracellular cysteine residues unpaired and available for intermolecular disulfide bonding (i.e., putative formation of a constitutively active, Δ16Her2 homodimer).

Δ16Her2 transcripts have been detected in a majority of breast tumors and reported to comprise 4-9% of total Her2 transcripts. The Δ16Her2 protein has been associated with trastuzumab (Herceptin®) resistance. And oncogenic transformation associated with wild-type Her2 overexpression may very well be a function of the associated increase in absolute levels of the Δ16Her2 protein to a critical threshold required for constitutive activation of the Her2 pathway by Δ16Her2 homodimer activity.

Pertinent to certain embodiments of the invention, a long form of a human prolactin receptor (alternatively called "PRLRlf" or "LF PRLR") protein is encoded by mRNA comprised of exons 1-10 of PRLR pre-mRNA (FIG. 8A) spliced together. And a short form human PRLR splice variant comprises exons 3-9 and 11 of human prolactin receptor short form 1b pre-mRNA (FIG. 9A) spliced together, and codes for a dominant negative form of human PRLR (see RefSeq database, accession number NM_000949, incorporated by reference herein). In some embodiments of the invention, PRLRlf mRNA can be advantageously modulated in a mammalian (e.g., a mouse or human) cell using SMOs.

Antimaia is the name we have given to our splice-modulating oligomer that inhibits expression of the LF prolactin receptor and by so doing increases the relative expression of the short form prolactin receptors. Human and mouse forms of Antimaia have the following sequences: GCCCTTCTATTAAAACACAGACACA (human); GCCCTTCTATTGAAACACAGATACA (mouse). The oligonucleotide is derivatized by adding morpholino groups to enhance half life and by octaguanidine groups to effect cell penetration.

The present invention may be better understood by referring to the accompanying examples, which are intended for illustration purposes only and should not in any sense be construed as limiting the scope of the invention.

Example 1

Pumps containing Antimaia were implanted into mice, and Antimaia was used at 1, 10 and 100 pmoles/hour/mouse for 5 days. As shown in FIGS. 9A-9C, Antimaia reduced production of the long form of the prolactin receptor in mammary gland, liver and ovary. A shown in FIGS. 10A-10D, Antimaia had no effect on the short prolactin receptor forms (called S1-3 in mouse) or a related receptor, the growth hormone receptor (GHR).

Example 2

Potential cancer drugs are typically tested by analyzing their ability to shrink a primary tumor. While shrinkage of primary tumors can be crucial for inoperable tumors, the vast majority of primary tumors are surgically excised. Moreover, patient death results from cells that escaped the primary tumor, becoming metastases. Also, sometimes cancer recurs years after an apparent cure, suggesting that some cancer stem cells were dormant and then re-activated. To determine the ability of SMOs to inhibit metastatic spread and kill cancer stem cells, two highly aggressive and metastatic models were used.

First Model

In the first model, mouse breast cancer cells are used in normal mice. This allows an assessment of the efficacy of treatment in a situation where there is a normal hormone and immune environment, both of which would be present in a patient.

A solution of the Antimaia oligonucleotide was placed in a pump that delivered a constant dose, and mice were checked for metastases at various time points. Primary tumors were formed in the breast, and natural metastases emanating from the primary tumor were followed. 4T1 cells are a syngeneic balb/c mouse breast cancer cell line. After suspension in matrigel, cells were injected into the mammary fat pads. Numbers of cells injected and time after injection before analysis varied with the experiment. Metastatic spread was quantified on the basis of tumor cell resistance to 6-thioguanine Normal cells are not resistant. Lung tissue was dissociated and the cells were plated in medium containing 6-thioguanine Only the tumor cells survive and form colonies. The number of colonies produced by cells derived from control mice and mice treated with Antimaia can then be counted.

Figure 11:
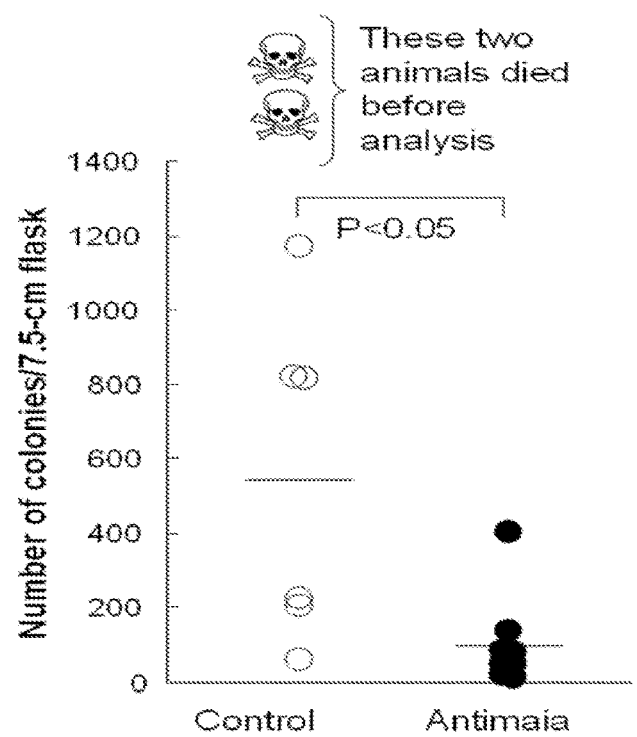
FIG. 11 is a graph of lung metastasis results of treated mice.

Results showed that Antimaia markedly reduced metastases to the lung at a time point (post 40 days) when metastatic spread was so bad that it killed two of the animals in the control group (FIG. 11).

Antimaia also decreased metastases in the liver and increased the immune response to tumor cells in the liver. Single cell suspensions were made from dissected livers and 1-2×$10^6$ cells in RPMI-1640 (plus 10% FBS+PenStrep) were incubated with 4T1 tumor cell lysate in the presence of purified mouse anti-CD28 antibody for an hour at 37° C./5% $CO_2$ humidified incubator, after which Golgi stop (monensin) was added and incubated for 5 hr. Cells were then washed and first stained with fluorochrome-conjugated rat anti-mouse CD4 antibody for T helper cells. After washing and permeabilization with fixation and permeabilization buffer, cells were stained for intracellular IFN-g and IL-2 with appropriate fluorochrome-conjugated rat anti-mouse IFN-g and anti-IL-2 antibodies. After staining, paraformaldehyde fixed cells were acquired in a BD FACSAria flow cytometer and analyzed by Flowjo software. Livers were also fixed in paraformaldehyde and stained with hematoxylin and eosin for routine histopathological analysis.

Figure 12:
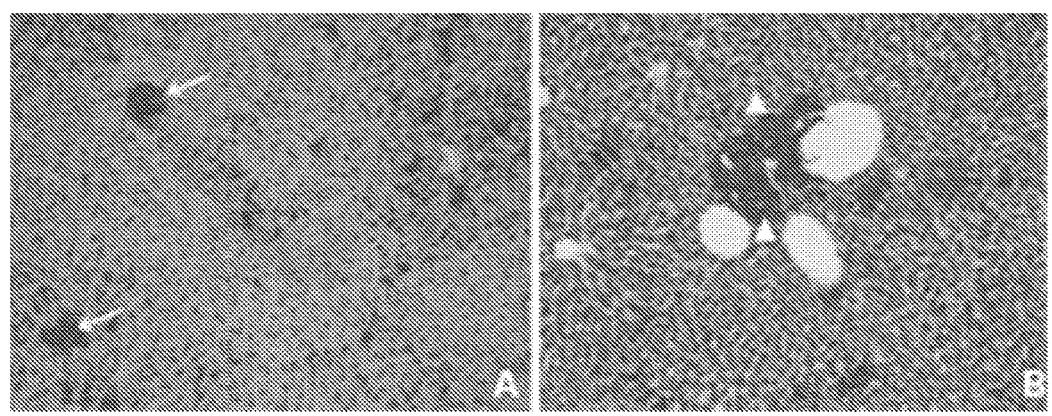
FIGS. 12A-12B are tissue section images from liver of control (12A) and treated (12B) mice.

As shown in FIGS. 12 A-12B, liver sections from control animals displayed metastases and poor tissue architecture (12A), while liver sections from Antimaia treated animals showed immune cell infiltration without signs of inflammatory destruction (12B).

Antimaia also increased the number of immune cells that are capable of killing tumor cells in the liver. Single cell suspensions were made from dissected livers and 1-2×10⁶ cells in RPMI-1640 (plus 10% FBS+PenStrep) were incubated with 4T1 tumor cell lysate in presence of purified mouse anti-CD28 antibody for an hour at 37° C./5% $CO_2$ humidified incubator, after which golgi stop monensin was added and incubated for 5 hr. Cells were then washed and first stained with fluorochrome conjugated rat anti-mouse CD8 antibody for effector cytotoxic T cells. After washing and permeabilization with fixation and permeabilization buffer, cells were stained for intracellular IFN-g and IL-2 with appropriate fluorochrome conjugated rat anti-mouse IFN-g and anti-IL-2 antibodies. After staining, paraformaldehyde fixed cells were acquired in BD FACSAria flow cytometer and analyzed by Flowjo software.

As shown in Table 1, Antimaia treatment increased the percentage of IL-2 positive CD8+ T cells in liver.

TABLE 1

Percentage T cells in the liver that produced IL-2 when exposed to tumor

| Animal No. | % CD4+(IL-2)+ | | % CD8+(IL-2)+ | |
|---|---|---|---|---|
| | Control | Antimaia | Control | Antimaia |
| 1 | 0 | 0 | 0 | 9.76 |
| 2 | ND | 1.75 | ND | 5.00 |
| 3 | ND | 0.741 | ND | 5.26 |
| 4 | 0 | 0 | 0 | 9.38 |
| 5 | 0 | 0.541 | 0 | 7.41 |
| 6 | 0.331 | 0.347 | 1.19 | 6.65 |
| 7 | 0 | 0 | 6.67 | 3.70 |
| 8 | 0 | 0 | 0 | 10.0 |
| Found: | 1/6 | 4/8 | 2/6 | 8/8 * |

ND: non detected because they died before taking sample.
* statistical significance compared to control (p < 0.01, Mann-Whitney test)

Figure 13:
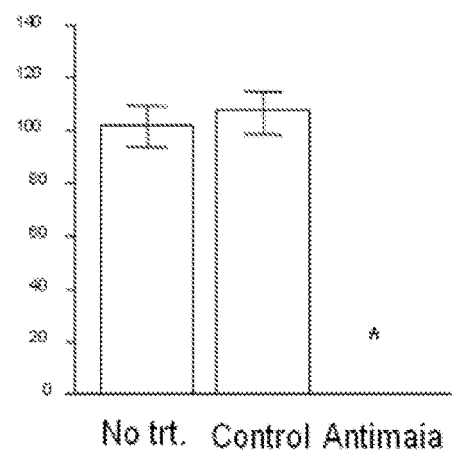
FIG. 13 is a graph of mammosphere results of treated mice.

Antimaia also reduced the number of cancer stem cells. Under experimental conditions, only stem cells survive and give rise to colonies greater than 50 μm in size. 4000 4T1 cells were cultured in serum free DMEM/F12 medium supplemented with 2% B27 and 20 ng/mL hEGF and plated in ultra-low attachment plates with either 1 uM control SMO or Antimaia or without treatment for 7 days. After 7 days, numbers of formed mammaosphperes bigger than 50 uμm were counted. Results are shown in FIG. 13.

Figure 14:
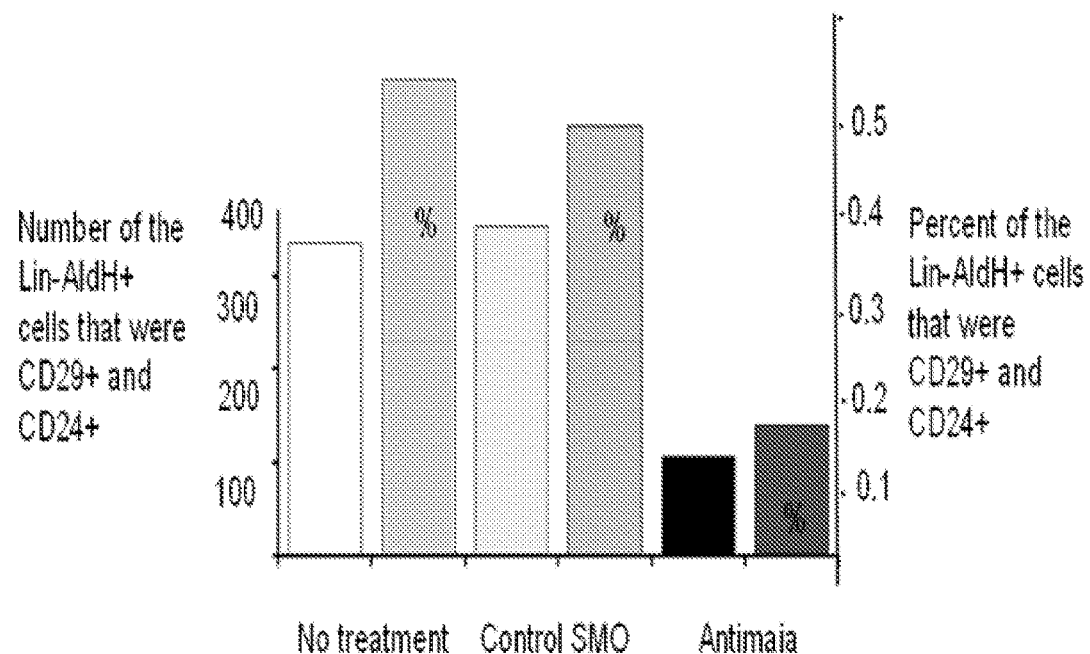
FIG. 14 is a graph of stem cell results of treated mice.

A second assay for stem cells gave similar results. 5×10⁵ 4T1 cells were seeded on plates and treated with 800 pmoles of control SMO or Antimaia per 8 hours or were without any treatment. Medium was changed every 8 hours for the entire 15-day experiment. The 15 day treatment was begun on day 1, the 9 day treatment started on day 7, the 5 day treatment started on day 11 and the 2 day treatment started on day 14 so that all samples were collected at the same time for flow cytometric analysis. To analyze the population of cancer stem cells, cells were stained with antibodies to Lin, CD24, CD29 and ALDH and the stem cells marked as Lin−/CD24+/CD29+/ALDH+ were gated. Results showed longer treatment with Antimaia decreased the population of cancer stem cells. Results from the 15 day treatment are shown in FIG. 14.

Second Model

Figure 15:
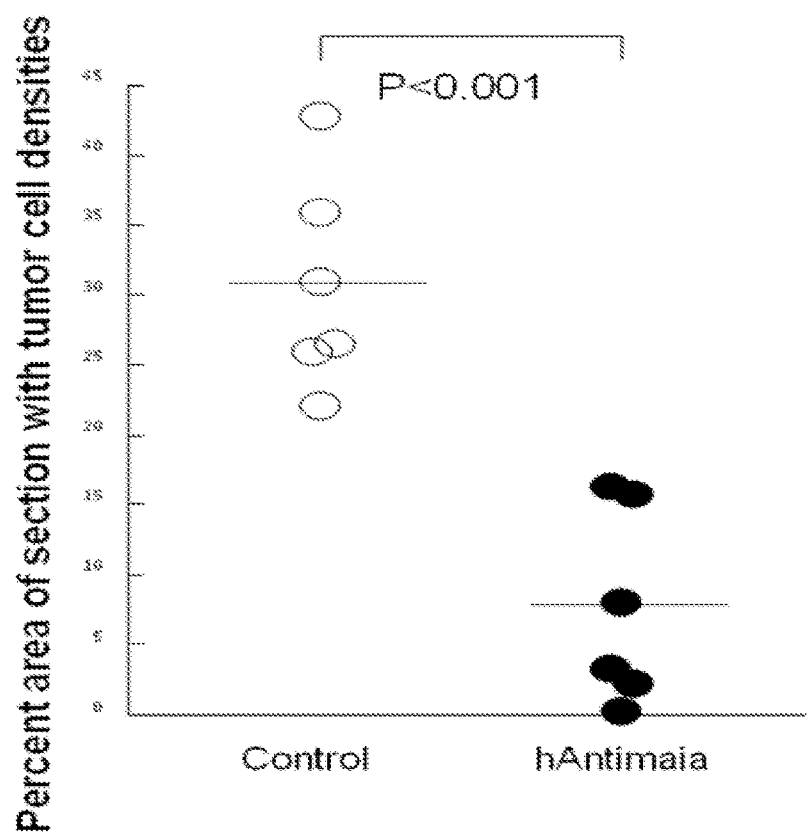
FIG. 15 is a graph of tumor cell densities of treated mice.

In the second model, human breast cancer cells were used in a mouse that would not reject the cancer because it has an impaired immune system. One million human BT474 cells were injected orthotopically into the mouse fat pad. The mice were treated with control SMO or human Antimaia for 25 days (100 pmoles/h/mouse) after which time the lungs were fixed for histopathological analysis of hematoxylin and eosin-stained sections. Morphometric analysis quantified the area of sections occupied by metastatic densities. As shown in FIG. 15, lungs of human-Antimaia treated animals showed markedly reduced metastatis.

Primary Tumor

Figure 16:
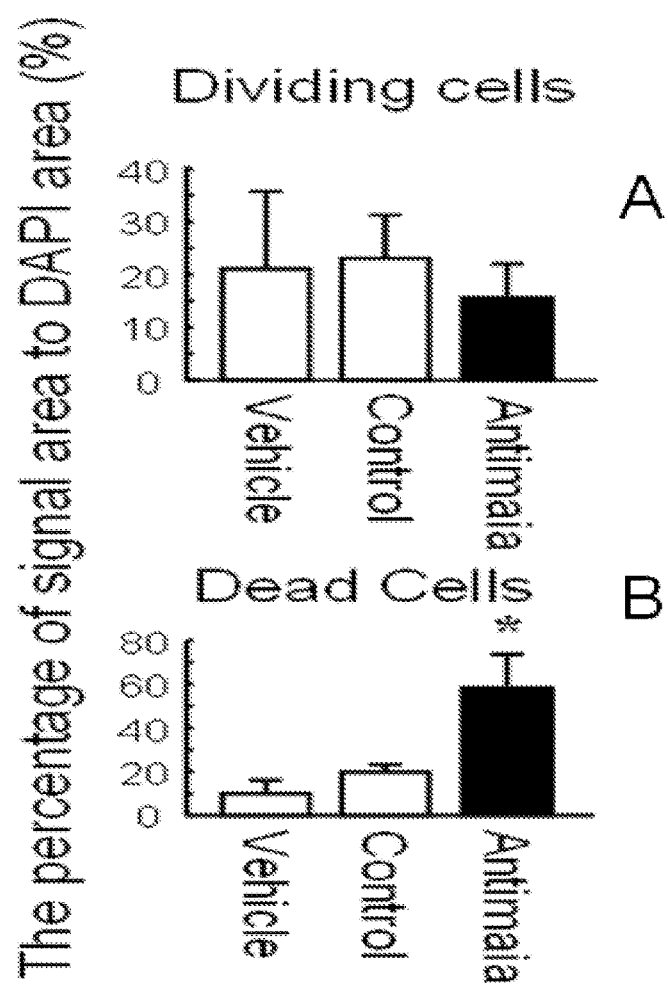
FIGS. 16A-16B are graphs of dividing cell (16A) and dead cell (16B) results of treated mice.

Antimaia also increased apoptosis and necrosis in the primary tumors. Three hours before sacrifice, tumor-bearing mice were injected with EdU (5-ethynyl-2'-deoxyuridine) that incorporates into DNA of dividing cells. Tumors formed by 4T1 cells in the mammary fat pad were fixed and processed for histopathology. Sections were stained for the presence of EdU and the percentage of positive dividing cells quantified by morphometric analysis. Sections were also stained to detect apoptosis using reagents that recognize cut ends of DNA produced by apoptosis. Results are shown in FIGS. 16A-16B.

Toxicity

Figure 17:
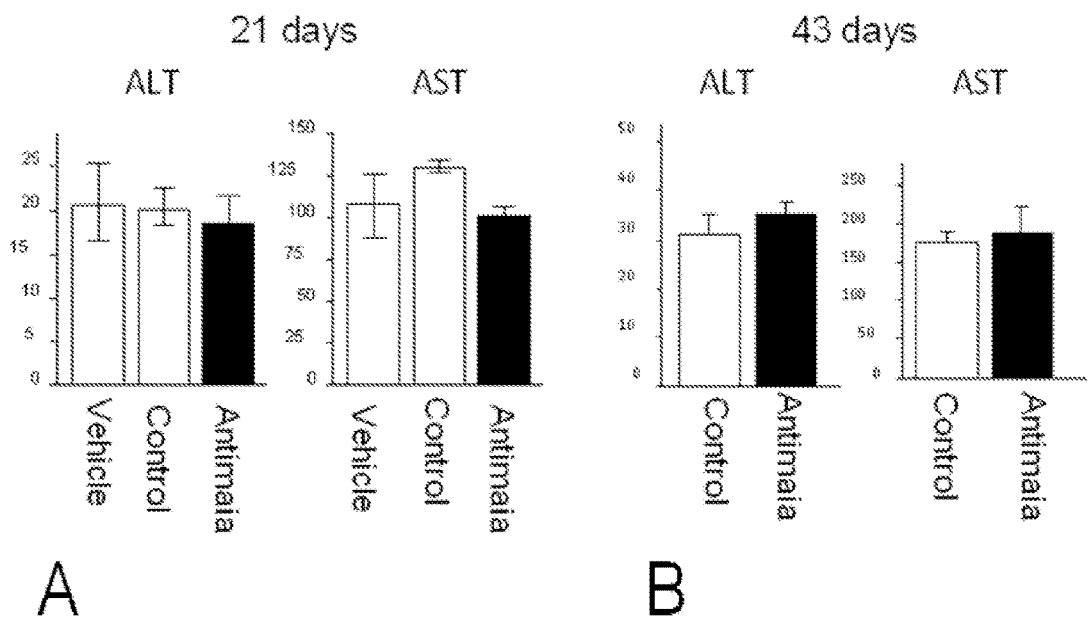
FIGS. 17A-17B are graphs of liver enzyme results at 21 days (17A) and 43 days (17B) of treated mice.

Analysis of liver enzymes in the blood, differential blood counts, and histological analysis of multiple tissues indicated that Antimaia showed no evidence of toxicity. Liver enzymes were analyzed using commercial clinical kits scaled down to accommodate sample size. Differential blood counts were performed on blood smears taken at the time of sacrifice. Histopathological analysis of routinely fixed and prepared tissues was performed on lung, heart, liver, and gastrointestinal tract/Results for liver enzymes are shown in FIGS. 17A-17B (ALT, alanine transaminase; AST, aspartate amino transferase).

Conclusions

Antimaia is predicted (based on charge considerations) not to cross the blood brain barrier and so would not be expected to affect cognition. In addition, Antimaia: has a major inhibitory effect on metastatic spread to the lungs and liver in both models; kills tumor cells by inducing apoptosis; in the normal mouse model, also stimulates an immune response to tumor cells; increased central primary tumor death; reduced the number of tumor stem cells, suggesting the possibility that it could eradicate all tumor cells; showed no toxic effects within the experimental time frames used.

Example 3

Figure 18:
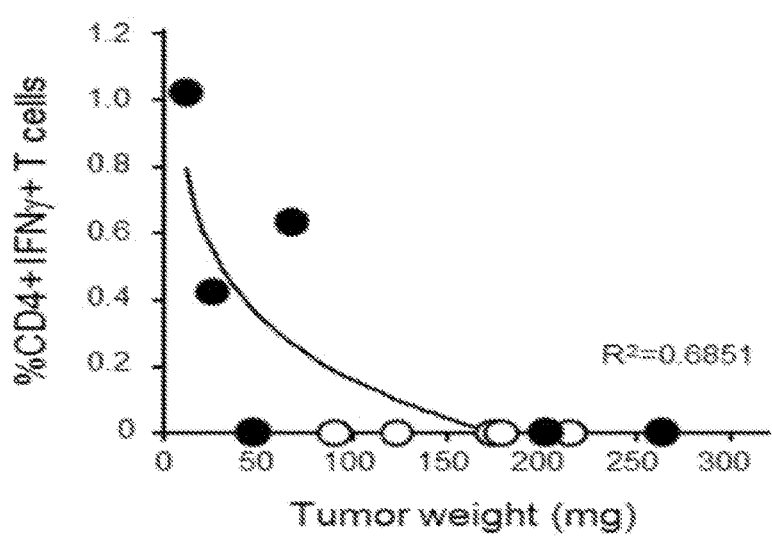
FIG. 18 is a graph showing tumor weight versus percentage of CD4+ effector cells in liver producing interferon gamma in response to tumor antigens ex vivo. Antimaia-treated animals are shown by filled circles and control animals by open circles. Analysis was after 1 month of treatment with antimaia or the chemically-similar control substance.

The inventors hypothesized that an observed reduction in tumor size and increased central death of tumors in the antimaia-treated group had an immunologic component and resulted, at least in part, from anti-tumor immunity by T cells. To test the hypothesis, isolated cells were isolated from liver (an organ with different grades of metastases) of the two groups of mice, and in ex vivo experiments, incubated the cells with lysed tumor cell (4T1) antigen (Ag)s, and detected any intracellular production of IFN-γ or IL-2 by T cells at the single cell level by multicolor flow cytometry. CD4+ T cells in three out of 6 in the antimaia group (3/6), but none (0/6) in the control group secreted IFN-γ in response to the tumor Ag with a percentage (%) range varying between (0.42%-1.02%, Mean 0.69+/−SD 0.3)— shown in FIG. 18. Similarly, four out of 6 (4/6) in the antimaia group secreted IL-2 in response to tumor Ag (% range: 0.22%-0.94%, Mean 0.61+/−SD 0.3) as compared to 1 in 6 (1/6) in the control group. Similarly, antigen-specific CD8+IL-2+ cells were present in three out of 6 (3/6) mice in the antimaia group (% range: 0.89%-1.1%, Mean 0.98+/−SD 0.11) as compared to 1 in 6 mice (1/6) in the control group. This analysis was conducted in a blinded fashion and then combined with the effect on tumor growth. At this point, failure in the delivery system for antimaia in two non-responding animals is suspected, but not proved. It is currently concluded that half of the antimaia-treated animals showed an immune response whereas none of the control animals did.

In conclusion, antimaia induces anti-tumor effector T cell immunity. This is the first demonstration that reduced expression of the LF prolactin receptor has such a beneficial effect on anti-tumor immunity.

Example 4

Antimaia (called PRLR SMO in Table 2) reduces T regulatory cell (Treg) recruitment to a tumor. Data is shown in Table 2. Balbc/J mice were implanted with an Alzet minipump containing Antimaia or Control SMO (same dose used in all in vivo experiments) and the next day were injected with $2 \times 10^6$ 4 T1 cells. At day 12, mice were sacrificed and the primary tumors were collected and digested with Accutase for 1.5 hour. Cells were then collected and stained with anti-CD4, CD25 and FOXP3 and analyzed by flow cytometry. Because Tregs reduce immune responses to tumor cells, fewer Tregs result in increased immune responses to the tumor.

TABLE 2

|  | Control | PRLR SMO |
| --- | --- | --- |
| Cells from primary tumor analyzed | 21835 | 24763 |
| CD4–CD25– cells | 20390 | 24404 |
| CD4+CD25– cells | 625 | 176 |
| CD4+CD25+ cells | 820 | 183 |
| CD4+CD25+FoxP3+ | 730 (3.3%) | 163 (0.66%) |

REFERENCES

The following publications are incorporated by reference herein:

1. Clancy, S. et al. Nature Education 1 (1) 92008) and Black, D. Annual Reviews of Biochemistry (2003) 72(1): 291-336.
2. Patel A. and Steitz J. Nat. Rev. Mol. Cell Biol. (2003) 4(12): 960-70.
3. Wang, E. et al. Nature (2008) 456:470-476.
4. Smirnova, O. et al. Biochemistry (Moscow) (2004) 69:351-363.
5. Hertel, K. et al. J Biol Chem (2008) 283:1211-1215.
6. Lin, S. et al. Adv Exp Med Biol (2007) 623:107-122.
7. Martinez-Contreras, R. et al. Adv Exp Med Biol (2007) 623:123-147.
8. K. Hung, R. Hayashi, A. Lafond-Walker, C. Lowenstein, D. Pardoll, and H. Levitsky, "The central role of CD4+ T cells in the antitumor immune response," J. Exp. Med., 188(12): 2357-2368, 1998.
9. A. Corthay, D. K. Skovseth, K. U. Lundin et al., "Primary antitumor immune response mediated by CD4+ T cells," Immunity, 22(3): 371-383, 2005.
10. A. Perez-Diez, N. T. Joncker, K. Choi et al., "CD4 cells can be more efficient at tumor rejection than CD8 cells," Blood, 109(12): 5346-5354, 2007.
11. K. Rakhra, P. Bachireddy, T. Zabuawala et al., "CD4+ T cells contribute to the remodeling of the microenvironment required for sustained tumor regression upon oncogene inactivation," Cancer Cell, 18(5): 485-498, 2010.
12. J. R. Schoenborn and C. B. Wilson. "Regulation of interferon-gamma during innate and adaptive immune responses". Adv. Immunol., 96: 41-101, 2007.
13. (K. A. Smith. "Interleukin-2: inception, impact, and implications". Science, 240(4856): 1169-1176, 1988.
14. P. Tijessen, "Hybridization with Nucleic Acid Probes" in Laboratory Techniques in Biochemistry and Molecular Biology, P. C. vand der Vliet, ed., c. 1993 by Elsevier, Amsterdam.
15. Tworoger S S, Eliassen A H, Sluss P, Hankinson S E. J Clin Oncol. 2007; 25(12):1482-8.
16. Clevenger C V, Chang W P, Ngo W, Pasha T L, Montone K T, Tomaszewski J E. Am J Pathol. 1995; 146(3):695-705.
17. Gill S, Peston D, Vonderhaar B K, Shousha S. J Clin Pathol. 2001 December; 54(12):956-60.
18. Greendale G A, Huang M H, Ursin G, Ingles S, Stanczyk F, Crandall C, Laughlin G A, Barrett-Connor E, Karlamangla A. Breast Cancer Res Treat. 2007 November; 105(3):337-46.
19. Boyd N F, Stone J, Martin L J, Jong R, Fishell E, Yaffe M, Hammond G, Minkin S. Br J Cancer. 2002 Oct. 7; 87(8):876-82.
20. Ben-Jonathan N, Mrshon J l, Allen D L, Steinmetz R W. Endocrine Rev 17:639-69.
21. Brandebourg T, Hugo E, Ben-Jonathan N. Diabetes Obes Metab 9:464-76.
22. Shemanko C S. Mammary epithelial stem and progenitor cells and the prolactin pathway. Front Biosci. 13:3940-50, 2008.
23. Clevenger C V, Gadd S l, Zheng J. Trends Endocrinol Metab 20: 223-9, 2009.
24. Pujianto D A, Curry B J, Aitken R J. Endocrinology 151:1269-79, 2010.
25. Ormandy C J, Binart N, Helleco C, Kelly P A., DNA Cell Biol 17:761-70, 1998.
26. Meng J, Tsai-Morris C H, Dufau M., Cancer Res 64:5677-82, 2004.
27. Huang K, Ueda E, Chen Y, Walker A M., J Mammary Gland Biol Neoplasia. 2008; 13(1):69-79.
28. Tan D, Walker A M., J Mol Endocrinology 44:187-94, 2010.
29. U.S. Pat. No. 4,469,863.
30. U.S. Pat. No. 5,750,666.
31. Sczakiel G (2000) Theoretical and experimental approaches to design effective antisense oligonucleotides. Front Biosci 5: D194-201.
32. Far R K, Leppert J, Frank K, Sczakiel G, (2005) Technical improvements in the computational target search for antisense oligonucleotides. Oligonucleotides 15: 223-233.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the invention and the following claims.

What is claimed is:

1. A method of treating cancer in a subject, in which cancer cells express a full length wild type polypeptide and an alternatively-spliced wild type dominant negative variant thereof, comprising
administering a splice modulating oligonucleotide to the subject in an amount effective to provide a therapeutic benefit to the subject,
wherein the oligonucleotide modifies splicing of a pre-mRNA encoding the full length wild type polypeptide and/or the wild type dominant negative variant thereof so as to reduce relative expression of the full length wild type polypeptide compared to expression of the wild type dominant negative variant, and
wherein the full length wild type polypeptide promotes cancer cell survival, proliferation, and/or metastasis, or promotes angiogenesis, or a combination thereof, and
the wild type dominant negative variant inhibits cancer cell survival, proliferation and/or metastasis, or inhibits angiogenesis, or a combination thereof,
wherein the cancer is breast cancer, prostate cancer or ovarian cancer, and
wherein the pre-mRNA is a prolactin receptor pre-mRNA, growth hormone receptor pre-mRNA, insulin receptor pre-mRNA, estrogen receptor α or β pre-mRNA, human epidermal growth factor receptor 2 (Her2) pre-mRNA, receptor tyrosine kinase ErbB4 pre-mRNA, or signal transducer and activator of transcription 5a (STAT5a) pre-mRNA.

2. A method of treating cancer in a subject, in which cancer cells express a full length wild type polypeptide and an alternatively-spliced wild type dominant negative variant thereof, comprising
administering a splice modulating oligonucleotide to the subject in an amount effective to provide a therapeutic benefit to the subject,
wherein the oligonucleotide modifies splicing of a pre-mRNA encoding the full length wild type polypeptide and/or the wild type dominant negative variant thereof so as to reduce relative expression of the full length wild type polypeptide compared to expression of the wild type dominant negative variant, and
wherein the full length wild type polypeptide promotes cancer cell survival, proliferation, and/or metastasis, or promotes angiogenesis, or a combination thereof, and
the wild type dominant negative variant inhibits cancer cell survival, proliferation and/or metastasis, or inhibits angiogenesis, or a combination thereof,
wherein the cancer is breast cancer, prostate cancer or ovarian cancer, and
wherein the full length wild type polypeptide is a full length prolactin receptor long form, a full length insulin receptor or an insulin receptor variant lacking exon 11, a full length estrogen receptor or an estrogen receptor α variant lacking exon 5, a full length Her2 polypeptide or a Her2 polypeptide variant lacking exon 16, or a full length STAT5a or a STAT5a polypeptide variant lacking exon 5.

3. The method of claim 2, wherein the amount is effective to increase apoptosis and/or necrosis of cancer cells; stimulate an anti-tumor T cell response, decrease Treg cell recruitment to a tumor associated with the cancer; decrease cancer stem cell numbers; or decrease cancer metastasis; or a combination thereof.

4. The method of claim 3, wherein the anti-tumor T cell response comprises increasing tumor-specific CD4+ T cells, tumor-specific CD8+ T cells, or both, in the subject.

5. The method of claim 2, wherein the oligonucleotide is complementary to an intron/exon junction, a 5' splice site, a 3' splice site, a branch site, an intronic splice enhancer, or an exonic splice enhancer, of the pre-mRNA.

6. A method of treating cancer in a subject, in which cancer cells express a full length wild type polypeptide and an alternatively-spliced wild type dominant negative variant thereof, comprising
    administering a splice modulating oligonucleotide to the subject in an amount effective to provide a therapeutic benefit to the subject,
    wherein the oligonucleotide modifies splicing of a pre-mRNA encoding the full length wild type polypeptide and/or the wild type dominant negative variant thereof so as to reduce relative expression of the full length wild type polypeptide compared to expression of the wild type dominant negative variant, and
    wherein the full length wild type polypeptide promotes cancer cell survival, proliferation, and/or metastasis, or promotes angiogenesis, or a combination thereof, and
    the wild type dominant negative variant inhibits cancer cell survival, proliferation and/or metastasis, or inhibits angiogenesis, or a combination thereof,
    wherein the cancer is breast cancer, prostate cancer or ovarian cancer, and
    wherein the cancer is a cancer involving prolactin and/or prolactin receptor.

7. The method of claim 6, wherein the cancer is breast cancer.

8. The method of claim 6, wherein the pre-mRNA is prolactin receptor pre-mRNA, and the full length wild type polypeptide is prolactin receptor long form.

9. The method of claim 6, wherein the oligonucleotide has the following sequence:

```
                                         (SEQ ID NO: 37)
GCCCTTCTATTAAAACACAGACACA
or
                                         (SEQ ID NO: 38)
GCCCTTCTATTGAAACACAGATACA.
```

10. A method of treating breast cancer in a subject, comprising administering a splice modulating oligonucleotide of the following sequence to the subject in an amount effective to provide a therapeutic benefit:

```
                                         (SEQ ID NO: 37)
GCCCTTCTATTAAAACACAGACACA
or
                                         (SEQ ID NO: 38)
GCCCTTCTATTGAAACACAGATACA.
```

11. The method of claim 10, wherein the amount is effective to increase apoptosis and/or necrosis of the breast cancer cells; stimulate an anti-tumor T cell response, decrease Treg cell recruitment to a tumor containing the breast cancer cells; decrease breast cancer stem cell numbers; or decrease breast cancer metastasis; or a combination thereof.

12. The method of claim 11, wherein the anti-tumor T cell response comprises increasing tumor-specific CD4+ T cells, tumor-specific CD8+ T cells, or both, in the subject.

13. A method of treating a disease involving prolactin or prolactin receptor, comprising:
    administering a splice modulating oligonucleotide to the subject in an amount effective to provide a therapeutic benefit, wherein the oligonucleotide modifies splicing of prolactin receptor pre-mRNA, wherein the oligonucleotide reduces expression of prolactin receptor long form, and wherein the oligonucleotide has the following sequence:

```
                                         (SEQ ID NO: 37)
GCCCTTCTATTAAAACACAGACACA
or
                                         (SEQ ID NO: 38)
GCCCTTCTATTGAAACACAGATACA.
```

14. The method of claim 13, wherein the disease is breast cancer, prostate cancer, ovarian cancer or lymphangioleiomyomatosis.

15. A splice modulating oligonucleotide of the following sequence:

```
                                         (SEQ ID NO: 37)
GCCCTTCTATTAAAACACAGACACA
or
                                         (SEQ ID NO: 38)
GCCCTTCTATTGAAACACAGATACA.
``` wherein the splice modulating oligonucleotide is a morpholino oligonucleotide or further comprises a modified oligonucleotide backbone.

16. A method of treating cancer in a subject, in which cancer cells express a full length wild type polypeptide and an alternatively-spliced wild type dominant negative variant thereof, comprising
    administering a splice modulating oligonucleotide to the subject in an amount effective to provide a therapeutic benefit to the subject,
    wherein the oligonucleotide modifies splicing of a pre-mRNA encoding the full length wild type polypeptide and/or the wild type dominant negative variant thereof so as to reduce relative expression of the full length wild type polypeptide compared to expression of the wild type dominant negative variant, and
    wherein the full length wild type polypeptide promotes cancer cell survival, proliferation, and/or metastasis, or promotes angiogenesis, or a combination thereof, and
    the wild type dominant negative variant inhibits cancer cell survival, proliferation and/or metastasis, or inhibits angiogenesis, or a combination thereof,
    wherein the cancer is breast cancer, prostate cancer or ovarian cancer, and
    wherein the wild type dominant negative variant is a prolactin receptor short form, a growth hormone receptor variant lacking part of exon 9 and all of exon 10, an estrogen receptor α variant lacking exon 7, an estrogen receptor β variant lacking exon 5, an ErbB4 kinase variant lacking exon 26.

17. The method of claim 1, wherein the therapeutic benefit is a reduction in cancer metastasis.

18. The method of claim 1, wherein the amount is effective to increase apoptosis and/or necrosis of cancer cells; stimulate an anti-tumor T cell response, decrease Treg cell recruitment to a tumor associated with the cancer; decrease cancer stem cell numbers; or decrease cancer metastasis; or a combination thereof.

19. The method of claim 18, wherein the anti-tumor T cell response comprises increasing tumor-specific CD4+ T cells, tumor-specific CD8+ T cells, or both, in the subject.

20. The method of claim 1, wherein the oligonucleotide is complementary to an intron/exon junction, a 5' splice site, a 3' splice site, a branch site, an intronic splice enhancer, or an exonic splice enhancer, of the pre-mRNA.

21. The method of claim 2, wherein the therapeutic benefit is a reduction in cancer metastasis.

22. The method of claim 6, wherein the amount is effective to increase apoptosis and/or necrosis of cancer cells; stimulate an anti-tumor T cell response, decrease Treg cell recruitment to a tumor associated with the cancer; decrease cancer stem cell numbers; or decrease cancer metastasis; or a combination thereof.

23. The method of claim 22, wherein the anti-tumor T cell response comprises increasing tumor-specific CD4+ T cells, tumor-specific CD8+ T cells, or both, in the subject.

24. The method of claim 6, wherein the oligonucleotide is complementary to an intron/exon junction, a 5' splice site, a 3' splice site, a branch site, an intronic splice enhancer, or an exonic splice enhancer, of the pre-mRNA.

25. The method of claim 6, wherein the therapeutic benefit is a reduction in cancer metastasis.

26. The method of claim 10, wherein the therapeutic benefit is a reduction in cancer metastasis.

27. The method of claim 16, wherein the amount is effective to increase apoptosis and/or necrosis of cancer cells; stimulate an anti-tumor T cell response, decrease Treg cell recruitment to a tumor associated with the cancer; decrease cancer stem cell numbers; or decrease cancer metastasis; or a combination thereof.

28. The method of claim 27, wherein the anti-tumor T cell response comprises increasing tumor-specific CD4+ T cells, tumor-specific CD8+ T cells, or both, in the subject.

29. The method of claim 16, wherein the oligonucleotide is complementary to an intron/exon junction, a 5' splice site, a 3' splice site, a branch site, an intronic splice enhancer, or an exonic splice enhancer, of the pre-mRNA.

30. The method of claim 16, wherein the therapeutic benefit is a reduction in cancer metastasis.

* * * * *

SEQUENCE LISTING

<160> NUMBER OF SEQ ID NOS: 38

<210> SEQ ID NO 1
<211> LENGTH: 439
<212> TYPE: RNA
<213> ORGANISM: Homo sapiens

<400> SEQUENCE: 1

| | | | | | |
|---|---|---|---|---|---|
| uacuugacuu | cacuauaaag | uauguucgua | uugcauuuac | uccaucuagu | agaaaauaga | 60 |
| ccuugucagu | ucaaaucccu | guugcauuaa | uuucaccagu | aaugagucuu | uuucauuuga | 120 |
| gucagcaggg | uuuuucuugc | uuguuuucag | gcuuugugga | uuugacccuc | caugaucagg | 180 |
| uccaccuucu | agaaugugcc | uggcuagaga | uccugaugau | uggucucguc | uggcgcucca | 240 |
| uggagcaccc | agggaagcua | cuguuugcuc | cuaacuugcu | cuuggacagg | uaagugaccu | 300 |
| ggcuguagcu | uaggaguagc | auguucuuua | cgaucauagu | ucaucauga | aacuauuuua | 360 |
| uucaucucuc | ggugaagcuu | cagagaacuu | uauuagguau | guuuacuuaa | caaaagagug | 420 |
| cauuggggu | gaugaagcc | | | | | 439 |

<210> SEQ ID NO 2
<211> LENGTH: 489
<212> TYPE: RNA
<213> ORGANISM: Homo sapiens

<400> SEQUENCE: 2

| | | | | | |
|---|---|---|---|---|---|
| cgguuuuaaa | uggguccaga | gcauccccau | ugcuagacua | cugugcugag | gaagggcacu | 60 |
| ggcucauugu | uacaucccau | gaacacucug | ggucuccuag | accucauccu | cuugagcuu | 120 |
| cucucucuca | cucucucucu | gcgcauucag | gaguguacac | auuucugucc | agcacccuga | 180 |
| agucucugga | agagaaggac | cauauccacc | gaguccugga | caagaucaca | gacacuuuga | 240 |
| uccaccugau | ggccaaggca | ggccugaccc | ugcagcagca | gcaccagcgg | cuggcccagc | 300 |
| uccuccucau | ccucucccac | aucaggcaca | ugaggugagg | caucuguggg | cuuccuacag | 360 |
| gagagacaua | aagaaaacau | gcccccaaac | cuaugugaca | gcuggccggg | aaggacuggu | 420 |
| gccugcauau | ggagagugca | cuugugacag | uuccuggcau | agaauaagca | uaaaugcuau | 480 |
| aggaggaca | | | | | | 489 |

<210> SEQ ID NO 3
<211> LENGTH: 50
<212> TYPE: RNA
<213> ORGANISM: Homo sapiens

<400> SEQUENCE: 3

| | | | | | |
|---|---|---|---|---|---|
| ucucacucuc | ucucugcgca | uucaggagug | uacacauuuc | uguccagcac | | 50 |

<210> SEQ ID NO 4
<211> LENGTH: 50
<212> TYPE: RNA
<213> ORGANISM: Homo sapiens

<400> SEQUENCE: 4

| | | | | | |
|---|---|---|---|---|---|
| uccucuccca | caucaggcac | augaggugag | gcaucugugg | gcuuccuaca | | 50 |

<210> SEQ ID NO 5
<211> LENGTH: 16
<212> TYPE: RNA
<213> ORGANISM: Homo sapiens

<400> SEQUENCE: 5

```
ugcuagacua cugugc                                                   16
```

<210> SEQ ID NO 6
<211> LENGTH: 67
<212> TYPE: RNA
<213> ORGANISM: Homo sapiens

<400> SEQUENCE: 6

```
ccaugaacac ucugggucuc cuagaccuca uccucuuuga gcuucucucu cucacucucu   60
cucugcg                                                            67
```

<210> SEQ ID NO 7
<211> LENGTH: 532
<212> TYPE: RNA
<213> ORGANISM: Homo sapiens

<400> SEQUENCE: 7

```
aaaaguuaug ucguugguuu ugcuaguacg gucacgacca uaguaaucuu ugguacgugc   60
cccacaggcu ccagaaaaua aagucaagc ugcuuuugcu ugacugcggu uuuacccugg   120
caauucgaau gacucugcuu uccucuucag gcucccggag agagaugu ggguaccgcc    180 uugugcggag acagagaagu gccgacgagc agcugcacug ugccggcaag gccaagagaa   240
guggcggcca cgcgccccga gugcgggagc ugcugcugga cgcccugagc ccgagcagc    300 uagugcucac ccuccuggag gcugaccgc cccaugugcu gaucagccgc ccagugcgc    360 ccuucaccga ggccuccaug augaugccg ugaccaaguu ggccgacaag gaguugguac   420
acaugaucag cugggccaag aagauccccg guagggcuuu cuggcuauca guuuccaug   480 uacuuguaga aaggccggcc gcuaauauuu aaggggcaag aguacaaagu ag          532
```

<210> SEQ ID NO 8
<211> LENGTH: 50
<212> TYPE: RNA
<213> ORGANISM: Homo sapiens

<400> SEQUENCE: 8

```
cgaaugacuc ugcuuuccuc uucaggcucc cggagagaga gauguggguu              50
```

<210> SEQ ID NO 9
<211> LENGTH: 50
<212> TYPE: RNA
<213> ORGANISM: Homo sapiens

<400> SEQUENCE: 9

```
aucagcuggg ccaagaagau ucccgguagg gcuuucuggc uaucaguuuu              50
```

<210> SEQ ID NO 10
<211> LENGTH: 8
<212> TYPE: RNA
<213> ORGANISM: Homo sapiens

<400> SEQUENCE: 10

```
cacgacca                                                            8
```

<210> SEQ ID NO 11
<211> LENGTH: 13
<212> TYPE: RNA
<213> ORGANISM: Homo sapiens

<400> SEQUENCE: 11

| | |
|---|---|
| ucugcuuucc ucu | 13 |

<210> SEQ ID NO 12
<211> LENGTH: 393
<212> TYPE: RNA
<213> ORGANISM: Homo sapiens

<400> SEQUENCE: 12

| | |
|---|---|
| acagagauau agaggugucu ggggauaguu ccugaggcuc ccugggaaaa gcugaggcag | 60 |
| aggcugaagg agaggaaggg cugggcauag caugggcug gcauggcugg agcagaggau | 120 |
| ggcgcuggag gcuacguug gauucuuuca gaaaacauau gaccgcugcc cccuggagcu | 180 |
| gguccgcugc auccggcaca ucuguacaa ugaacagagg cugguccgag aagccaacaa | 240 |
| ugugaguguc ccuuggggau ggggaggagu guugagaagu ccuccauau gccuuucucu | 300 |
| ccagaaacaa cuguguuuau auaaaacagc agcacgagga gagcaccaag aagaugaggg | 360 |
| acgugggcaa guguaagagg uggcagcauu gca | 393 |

<210> SEQ ID NO 13
<211> LENGTH: 25
<212> TYPE: RNA
<213> ORGANISM: Homo sapiens

<400> SEQUENCE: 13

| | |
|---|---|
| ggggcacuac gccacgcagc uccag | 25 |

<210> SEQ ID NO 14
<211> LENGTH: 25
<212> TYPE: RNA
<213> ORGANISM: Homo sapiens

<400> SEQUENCE: 14

| | |
|---|---|
| ugcagcucuc cggcugggau ccugg | 25 |

<210> SEQ ID NO 15
<211> LENGTH: 391
<212> TYPE: RNA
<213> ORGANISM: Homo sapiens

<400> SEQUENCE: 15

| | |
|---|---|
| ucauaaaaca gaaaaaaacu aagucguugc auucuguuuc agugguuauc aagagaaauc | 60 |
| acugacuuua uuagaugaau acaaauuaug aauuuuuugu gaaaagggaa agggaaaugu | 120 |
| aaacugugcu ucaacuauuc guaauucuga auuucuacuu uccauggcuc uuaauuauua | 180 |
| ucuuuggaau auuugggcua acagugaugc uauuguauu cuuauuuucu aaacagcaaa | 240 |
| gguaggugug gaguaguauu cuuuggauau uguaccagu uguuuagauu ccauaugug | 300 |
| uuucuauuug uuauuugaua uuuucuuugu caaauuauga guggaaauuu uaguuaaccu | 360 |
| aguacacuuu uaucuccagu uauauauuua c | 391 |

<210> SEQ ID NO 16
<211> LENGTH: 370
<212> TYPE: RNA
<213> ORGANISM: Homo sapiens

<400> SEQUENCE: 16

| | |
|---|---|
| uaguuguucu uuuuuuuccu ucuacaguuu ucuuucuca uuuacugucu aauauuucu | 60 |
| ucuguuucuc acacuccaau uauauaaagu accagauauu uggaaaaag uaauaguauu | 120 |
| gccaauauuu uauuucuauc uuuugcuaua gauuaaaaug cugauucugc ccccaguucc | 180 |

```
aguuccaaag auuaaaggaa ucgauccaga ucuccucaag guaacuaaua auuuuaucua      240
aauuguagcu aguacuaauu aacaccugaa gacuccuguc auauguugaa gguuuucugu      300
aagcuauaua uaucacauuc aauuuucuug ugucucuucu ccuggagaaa auuuuuuaa       360 auauucauu                                                             370

<210> SEQ ID NO 17
<211> LENGTH: 50
<212> TYPE: RNA
<213> ORGANISM: Homo sapiens

<400> SEQUENCE: 17
aaccaaaauu uuauauguuu ucaaggauua aaaugcugau ucugcccca                   50

<210> SEQ ID NO 18
<211> LENGTH: 348
<212> TYPE: RNA
<213> ORGANISM: Homo sapiens

<400> SEQUENCE: 18
auugugcugc uuaggaagcu ucacuguugu gcacuuuuuc cccuuugguu cauacgaccc       60
auguggcuuu ucuuuuucgu uucuuuuuuu aauuuuuuca uucauauugc cucuuauau       120 auccaucauu ccauuuuucu uuccuauuag agugaaauug gacacagccc uccuccugcc     180 uacacccca ugucaggagu aaguauuuca caaucaaccu ucaucuuuua ggauuuucgg      240
ucuuugcuua ccauguuucc ucucucgucu cugcauaaau uccucauuuu gccuugcca      300 acagugaguu aagaauuugg guacaucgu guagcugccu uuguagau                   348

<210> SEQ ID NO 19
<211> LENGTH: 48
<212> TYPE: RNA
<213> ORGANISM: Homo sapiens

<400> SEQUENCE: 19
ucauuccauu uuucuuuccu auuagaguga aauuggacac agcccucc                   48

<210> SEQ ID NO 20
<211> LENGTH: 50
<212> TYPE: RNA
<213> ORGANISM: Homo sapiens

<400> SEQUENCE: 20
uccugccuac accccaugu caggaguaag uauuucacaa ucaaccuuca                  50

<210> SEQ ID NO 21
<211> LENGTH: 21
<212> TYPE: RNA
<213> ORGANISM: Homo sapiens

<400> SEQUENCE: 21
ggcuuuucuu uuucguuucu u                                                21

<210> SEQ ID NO 22
<211> LENGTH: 18
<212> TYPE: RNA
<213> ORGANISM: Homo sapiens

<400> SEQUENCE: 22
ucauucauau ugccucuu                                                    18
```

<210> SEQ ID NO 23
<211> LENGTH: 20
<212> TYPE: RNA
<213> ORGANISM: Homo sapiens

<400> SEQUENCE: 23
ccaucauucc auuuuucuuu                                                    20

<210> SEQ ID NO 24
<211> LENGTH: 336
<212> TYPE: DNA
<213> ORGANISM: Homo sapiens

<400> SEQUENCE: 24
ccugcaccug cugggaaga uguagcucac uccgucuagc aagugauggg agcgaguggu         60 ccaggucaa agccaggguɡ cccuuacucg gacacaugug gccuccaagu gucagagccc        120
aguggucugu cuaaugaagu ucccucuguc aaaaaccucu ucaggcacug gugccgagga       180
cccuagguau gacucaccug ugcgaccccu ggugccugcu ccgcgcaggg ccggcggcgu       240
gccaggcaga ugccucggag aacccagggg uuucuguggc uuuuugcaug cggcgggcag       300
cugugcugga gagcagaugc uucaccaauu cagaaa                                 336

<210> SEQ ID NO 25
<211> LENGTH: 25
<212> TYPE: RNA
<213> ORGANISM: Homo sapiens

<400> SEQUENCE: 25
ugcacaacgu gguuuucguc cccag                                              25

<210> SEQ ID NO 26
<211> LENGTH: 25
<212> TYPE: RNA
<213> ORGANISM: Homo sapiens

<400> SEQUENCE: 26
gccaucucgg aaacgcaggu cccuu                                              25

<210> SEQ ID NO 27
<211> LENGTH: 336
<212> TYPE: RNA
<213> ORGANISM: Homo sapiens

<400> SEQUENCE: 27
ccugcaccug cugggaaga uguagcucac uccgucuagc aagugauggg agcgaguggu         60 ccaggucaa agccaggguɡ cccuuacucg gacacaugug gccuccaagu gucagagccc        120
aguggucugu cuaaugaagu ucccucuguc aaaaaccucu ucaggcacug gugccgagga       180
cccuagguau gacucaccug ugcgaccccu ggugccugcu ccgcgcaggg ccggcggcgu       240
gccaggcaga ugccucggag aacccagggg uuucuguggc uuuuugcaug cggcgggcag       300
cugugcugga gagcagaugc uucaccaauu cagaaa                                 336

<210> SEQ ID NO 28
<211> LENGTH: 311
<212> TYPE: RNA
<213> ORGANISM: Homo sapiens

<400> SEQUENCE: 28
ggaggaggug gaggaggagg gcugcuugag gaaguauaag aaugaaguug ugaagcugag        60

```
auuccccucc auugggaccg gagaaaccag gggagccccc cggggcagccg cgcgccccuu    120 cccacggggc ccuuuacugc gccgcgcgcc cggccccac cccucgcagc accccgcgcc     180
ccgcgcccuc ccagccgggu ccagccggag ccauggggcc ggagccgcag ugagcaccau    240
ggagcuggcg gccuugugcc gcuggggggcu ccccucgcc cucuugcccc ccggagccgc    300
gagcacccaa g                                                         311
```

<210> SEQ ID NO 29
<211> LENGTH: 50
<212> TYPE: RNA
<213> ORGANISM: Homo sapiens

<400> SEQUENCE: 29

```
uggggccgga gccgcaguga gcaccaugga gcuggcggcc uugugccgcu              50
```

<210> SEQ ID NO 30
<211> LENGTH: 25
<212> TYPE: RNA
<213> ORGANISM: Homo sapiens

<400> SEQUENCE: 30

```
cuugccccau caacugcacc cacuc                                          25
```

<210> SEQ ID NO 31
<211> LENGTH: 25
<212> TYPE: RNA
<213> ORGANISM: Homo sapiens

<400> SEQUENCE: 31

```
cccucugacg uccaucaucu cugcg                                          25
```

<210> SEQ ID NO 32
<211> LENGTH: 300
<212> TYPE: RNA
<213> ORGANISM: Homo sapiens

<400> SEQUENCE: 32

```
aaggugauuc uagauggccu ggcacacaaa ugucugaagu uugagaucuu cccaccugcu    60
uguggcaaug aacagcacca cuuagcaggg augcugauuu ggaauguuau gaagcuaaca   120
gccaucucuu cuugugucug uguuuuaaua gaagggcaag ucugaagaac uacgagaguc   180
cuugggaugc caagacuuuc cucccacuuc ugacuaugag gacuugcugg uggaguauuu   240
agaaguagau gauagugagg accagcaucu aaugucaguc cauucaaaag aacacccaag   300
```

<210> SEQ ID NO 33
<211> LENGTH: 25
<212> TYPE: RNA
<213> ORGANISM: Homo sapiens

<400> SEQUENCE: 33

```
ugugucugug uuuuaauaga agggc                                          25
```

<210> SEQ ID NO 34
<211> LENGTH: 8
<212> TYPE: RNA
<213> ORGANISM: Homo sapiens

<400> SEQUENCE: 34

```
cuugaguu                                                             8
```

```
<210> SEQ ID NO 35
<211> LENGTH: 8
<212> TYPE: RNA
<213> ORGANISM: Homo sapiens

<400> SEQUENCE: 35 cccucuag                                                                   8

<210> SEQ ID NO 36
<211> LENGTH: 11
<212> TYPE: RNA
<213> ORGANISM: Homo sapiens

<400> SEQUENCE: 36
guacuguuuu u                                                              11

<210> SEQ ID NO 37
<211> LENGTH: 25
<212> TYPE: DNA
<213> ORGANISM: Artificial Sequence
<220> FEATURE:
<223> OTHER INFORMATION: synthetic oligonucleotide to human sequence

<400> SEQUENCE: 37
gcccttctat taaaacacag acaca                                               25

<210> SEQ ID NO 38
<211> LENGTH: 25
<212> TYPE: DNA
<213> ORGANISM: Artificial Sequence
<220> FEATURE:
<223> OTHER INFORMATION: synthetic oligonucleotide to mouse sequence

<400> SEQUENCE: 38
gcccttctat tgaaacacag ataca                                               25
```